US012165774B1

(12) United States Patent
Agarwal et al.

(10) Patent No.: US 12,165,774 B1
(45) Date of Patent: Dec. 10, 2024

(54) METHOD AND APPARATUS FOR PREDICTING PULSED FIELD ABLATION DURABILITY

(71) Applicant: Neutrace, Inc., Longwood, FL (US)

(72) Inventors: Animesh Agarwal, San Francisco, CA (US); Anand Ramani, Pleasanton, CA (US); Rohit Jain, Danville, CA (US)

(73) Assignee: Anumana, Inc., Cambridge, MA (US)

( * ) Notice: Subject to any disclaimer, the term of this patent is extended or adjusted under 35 U.S.C. 154(b) by 0 days.

(21) Appl. No.: 18/646,991

(22) Filed: Apr. 26, 2024

(51) Int. Cl.
  *G16H 50/70* (2018.01)
  *A61B 5/361* (2021.01)
  *G16H 50/20* (2018.01)

(52) U.S. Cl.
  CPC ............. *G16H 50/70* (2018.01); *A61B 5/361* (2021.01); *G16H 50/20* (2018.01)

(58) Field of Classification Search
  CPC ......... A61B 5/361; G16H 50/20; G16H 50/70
  See application file for complete search history.

(56) References Cited

U.S. PATENT DOCUMENTS

| | | | | |
|---|---|---|---|---|
| 11,564,591 B1* | 1/2023 | Narayan | ................ | G16H 30/40 |
| 2019/0104962 A1* | 4/2019 | Ghoraani | ............ | A61B 5/7282 |
| 2021/0212755 A1* | 7/2021 | Jimenez | ................ | A61B 5/6856 |
| 2021/0391082 A1* | 12/2021 | Amos | ................... | G06V 10/443 |
| 2022/0005198 A1* | 1/2022 | Goldberg | ............... | A61B 5/364 |
| 2022/0175447 A1* | 6/2022 | Fedewa | ............. | A61B 18/1206 |
| 2022/0248956 A1* | 8/2022 | Haeusser | ................ | A61B 5/742 |
| 2022/0344025 A1* | 10/2022 | Bort | ........................ | A61B 5/341 |
| 2022/0400951 A1* | 12/2022 | Haeusser | ................ | A61B 5/341 |
| 2023/0086307 A1* | 3/2023 | Sivaswamy | ........... | G06F 16/215 |
| | | | | 711/154 |
| 2023/0255684 A1* | 8/2023 | Schmidt | ............. | A61B 18/1492 |
| | | | | 606/41 |
| 2024/0112819 A1* | 4/2024 | Paamand | ................ | G16H 20/40 |
| 2024/0189032 A1* | 6/2024 | Zoubi | ................ | A61B 18/1492 |

FOREIGN PATENT DOCUMENTS

| | | |
|---|---|---|
| CN | 116230225 A | 6/2023 |
| CN | 116570360 A | 8/2023 |
| WO | 2022226227 A1 | 10/2022 |

OTHER PUBLICATIONS

O. Razeghi et al; "Atrial fibrillation ablation outcome prediction with a machine learning fusion framework incorporating cardiac computed tomography" J Cardiovasc Electrophysiol. May 2023; 34(5): 1164-1174.

* cited by examiner

*Primary Examiner* — Christopher A Flory
(74) *Attorney, Agent, or Firm* — Caldwell Intellectual Property Law

(57) ABSTRACT

Described herein is an apparatus and method for predicting Pulsed Field Ablation (PFA) durability. An apparatus may include at least a processor; and a memory communicatively connected to the at least processor, wherein the memory contains instructions configuring the at least processor to receive a training dataset comprising a plurality of example PFA device parameters correlated to a plurality of example PFA outcomes; train a PFA durability machine learning model using the training dataset; receive a PFA device parameter; and generate a PFA durability datum as a function of the PFA device parameter using a trained PFA durability machine learning model.

20 Claims, 8 Drawing Sheets

METHOD AND APPARATUS FOR PREDICTING PULSED FIELD ABLATION DURABILITY

FIELD OF THE INVENTION

The present invention generally relates to the field of pulsed field ablation. In particular, the present invention is directed to a method and apparatus for predicting pulsed field ablation durability.

BACKGROUND

Atrial fibrillation (AFib) is the most common arrhythmia in adults and affects a large amount of the adult population. The incidence and prevalence of AFib are increasing in association with aging of the population. Either medications or ablation procedures can be utilized to minimize the burden of AFib. Pulsed Field Ablation (PFA) is a relatively new method of performing cardiac ablation. Unlike RF ablation or cryo-ablation, PFA causes programed cell death. Additionally, PFA is believed to have the potential to be tissue selective, unlike RF and cryo-ablation. However, parameters and dosage of PFA have yet to be understood as well as RF and cryo-ablation parameters.

SUMMARY OF THE DISCLOSURE

In an aspect, an apparatus for predicting Pulsed Field Ablation (PFA) durability may include at least a processor; and a memory communicatively connected to the at least processor, wherein the memory contains instructions configuring the at least processor to receive a training dataset comprising a plurality of example PFA device parameters correlated to a plurality of example PFA outcomes; train a PFA durability machine learning model using the training dataset; receive a PFA device parameter; and generate a PFA durability datum as a function of the PFA device parameter using a trained PFA durability machine learning model.

In another aspect, a method of predicting Pulsed Field Ablation (PFA) durability may include, using at least a processor, receiving a training dataset comprising a plurality of example PFA device parameters correlated to a plurality of example PFA outcomes; using the at least a processor, training a PFA durability machine learning model using the training dataset; using the at least a processor, receiving a PFA device parameter; and using the at least a processor, generating a PFA durability datum as a function of the PFA device parameter using a trained PFA durability machine learning model.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for predicting Pulsed Field Ablation (PFA) durability. Cardiac ablations may be used to treat, in a non-limiting example, atrial fibrillation (AFib). Apoptosis may make it more difficult to determine durability of an ablation procedure. In some cases, AFib will resolve during a PFA procedure and then the tissue will heal and AFib returns. Some embodiments of the present disclosure use machine learning processes to predict the durability of a PFA procedure using outcome data from historical PFAs. In some embodiments, a system or method described herein may be performed using data on potential PFA device settings before a PFA procedure is performed. This may be used to select optimal PFA device settings for a procedure and/or predict PFA durability based on the input data, which was previously not possible.

Figure 1:
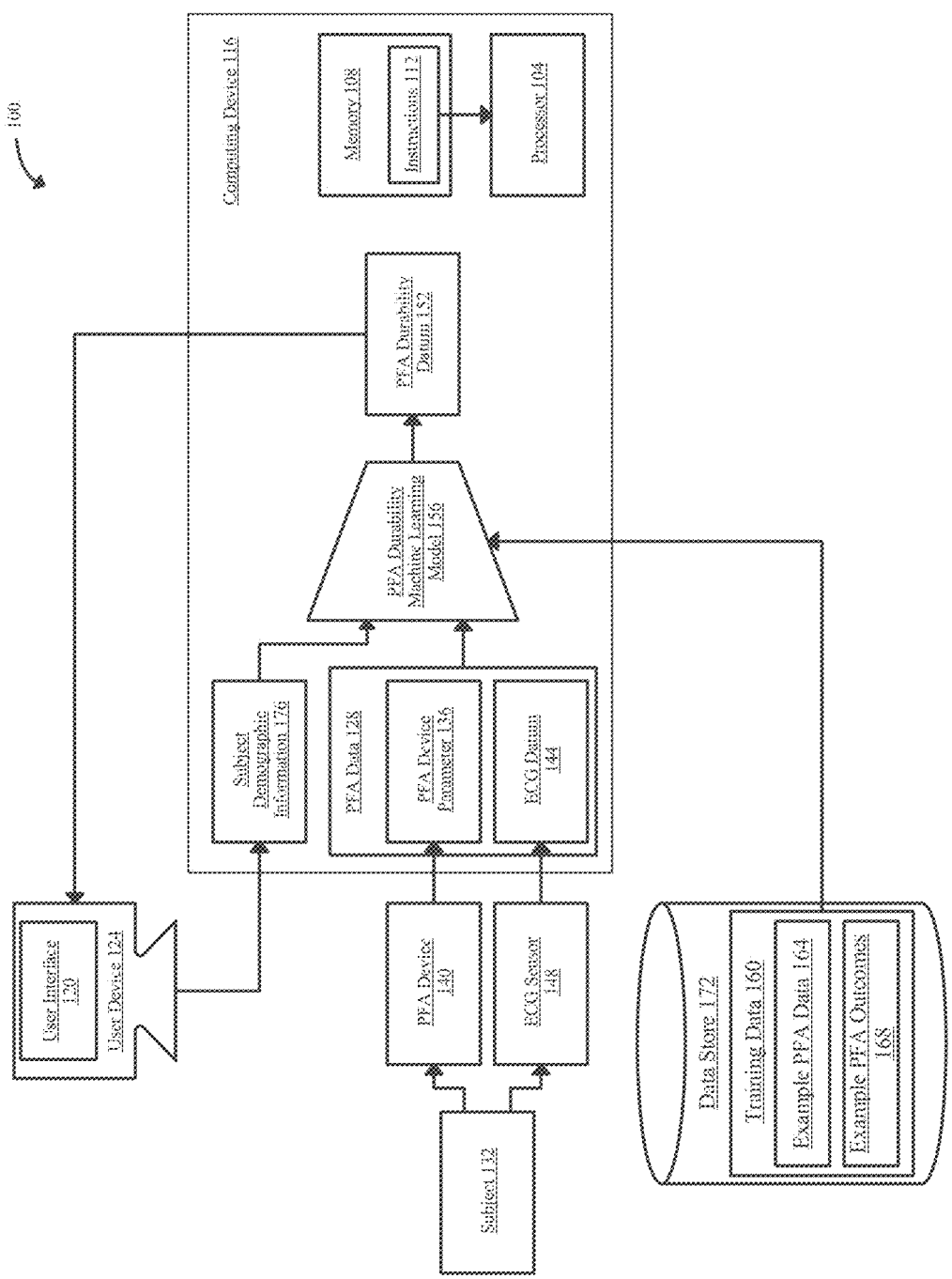
FIG. 1 is a diagram depicting an exemplary embodiment of an apparatus for predicting Pulsed Field Ablation (PFA) durability.

Referring now to FIG. 1, an exemplary embodiment of an apparatus 100 for predicting Pulsed Field Ablation (PFA) durability is illustrated. Apparatus 100 may include a computing device. Apparatus 100 may include a processor. Processor may include, without limitation, any processor described in this disclosure. Processor may be included in computing device. Computing device may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device may include a single computing device operating independently, or may include two or more computing device operating in concert, in parallel, sequentially or the like; two or more computing devices may be included together in a single computing device or in two or more computing devices. Computing device may interface or communicate with one or more additional devices as described below in further detail via a network interface device. Network interface device may be utilized for connecting computing device to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device.

Still referring to FIG. 1, in some embodiments, apparatus 100 may include at least a processor 104 and a memory 108 communicatively connected to the at least a processor 104, the memory 108 containing instructions 112 configuring the at least a processor 104 to perform one or more processes described herein. Computing device 116 may include processor 104 and/or memory 108. Computing device 116 may be configured to perform one or more processes described herein.

Still referring to FIG. 1, computing device 116 may include but is not limited to, for example, a computing device or cluster of computing devices in a first location and a second computing device or cluster of computing devices in a second location. Computing device 116 may include one or more computing devices dedicated to data storage, security, distribution of traffic for load balancing, and the like. Computing device 116 may distribute one or more computing tasks as described below across a plurality of computing devices of computing device, which may operate in parallel, in series, redundantly, or in any other manner used for distribution of tasks or memory between computing devices. Computing device 116 may be implemented, as a non-limiting example, using a "shared nothing" architecture.

Still referring to FIG. 1, computing device 116 may be designed and/or configured to perform any method, method step, or sequence of method steps in any embodiment described in this disclosure, in any order and with any degree of repetition. For instance, computing device 116 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 116 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, as used in this disclosure, "communicatively connected" means connected by way of a connection, attachment or linkage between two or more relate which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

Still referring to FIG. 1, in some embodiments, apparatus 100 includes user interface 120. User interface 120 may be a component of user device 124. User device 124 may include, in non-limiting examples, a smartphone, smartwatch, laptop computer, desktop computer, virtual reality device, or tablet. User interface 120 may include an input interface and/or an output interface. An input interface may include one or more mechanisms for a computing device to receive data from a user such as, in non-limiting examples, a mouse, keyboard, button, scroll wheel, camera, microphone, switch, lever, touchscreen, trackpad, joystick, and controller. An output interface may include one or more mechanisms for a computing device to output data to a user such as, in non-limiting examples, a screen, speaker, and haptic feedback system. An output interface may be used to display one or more elements of data described herein. As used herein, a device "displays" a datum if the device outputs the datum in a format suitable for communication to a user. For example, a device may display a datum by outputting text or an image on a screen or outputting a sound using a speaker.

Still referring to FIG. 1, in some embodiments, apparatus 100 receives PFA data. As used herein, "PFA data" is medical data of a subject which undergoes PFA, including PFA device parameters. PFA includes the delivery of rapid high voltage pulsed electrical fields to tissue, such as cardiac tissue. This may cause electroporation of cell membranes in the affected tissue. In some embodiments, PFA may include irreversible electroporation, in which pores are created in cell membranes, leading to cell death. In some embodiments, the strength of the effect applied may be controlled such that only target tissues are destroyed, and not surrounding tissues. In some embodiments, surrounding tissues around a target tissue may have higher thresholds for damage from electroporation. PFA may be applied to subject 132, and PFA data 128 of subject 132 may be determined. In some embodiments, PFA may be applied in subject 132 with Atrial Fibrillation (AFib).

Still referring to FIG. 1, in some embodiments, PFA data 128 may include PFA device parameter 136. As used herein, a "PFA device parameter" is an input variable that can be used to control output of a PFA device. As used herein, a "PFA device" is a device used to perform pulse field ablation of tissue, e.g., cardiac tissue. Non-limiting examples of PFA device 140 include the FARAPULSE PFA System (Boston Scientific) and PulseSelect (Medtronic). Non-limiting examples of PFA device parameters include voltage, pulse duration, frequency, pulse width, amplitude, power of ablation, total energy delivered, total treatment time, energy delivered to a particular location, treatment time at a particular location, current, average power, peak power, and pulse delivery phase (e.g., biphasic vs monophasic pulse delivery). In some embodiments, a PFA device parameter may be selected from the list consisting of voltage, pulse duration, frequency, pulse width, amplitude, power of ablation, total energy delivered, total treatment time, energy delivered to a particular location, treatment time at a particular location, current, average power, peak power, and biphasic vs monophasic pulse delivery. In some embodiments, PFA data 128 may include a PFA device identifier. As used herein, a "PFA device identifier" is a representation of a type of PFA device used to perform PFA in a subject. In some embodiments, PFA data 128 may include an electrode configuration used to apply PFA. In some embodiments, PFA data 128 may include a location of one or more electrodes during PFA. In some embodiments, PFA device parameter 136 may include a parameter that has been used, is about to be used, and/or could be used at a PFA device. In some embodiments, computing device 116 may receive from PFA device 140 PFA device parameter 136. In some embodiments, computing device 116 may input into PFA device 140 a PFA device parameter. For example, a PFA device parameter may be generated, optimized and/or modified based on a function described herein, and a result may be transmitted to PFA device 140 for use in a PFA procedure.

Still referring to FIG. 1, in some embodiments, PFA data 128 may include electrocardiogram (ECG) datum 144. As used herein, an "ECG datum" is a datum describing electrical activity of a heart. Likewise, "ECG data" is data describing electrical activity of a heart. In some embodiments, an ECG datum may include a rhythm strip ECG datum. As used herein, a "rhythm strip ECG datum" is a datum describing electrical activity detected using a single electrode. In some embodiments, an ECG datum may include a median beat ECG datum. As used herein, a "median beat ECG datum" is a datum describing electrical activity detected using a plurality of leads and/or electrodes. In some embodiments, ECG datum 144 may include data collected by 2, 3, 4, 5, 6, 7, 8, 9, 10, 11, 12, or more ECG leads. For example, ECG datum 144 may include a median beat collected by 12 ECG leads. In some embodiments, ECG datum 144 may be associated with subject 132. In some embodiments, ECG datum 144 may be detected and/or recorded using ECG sensor 148. ECG sensor 148 may include one or more electrodes. Electrodes may be placed on subject 132 such as on chest, arms, and legs of subject 132. Electrodes may detect electrical impulses produced by the heart. Lead wires may be used to connect electrodes to a computing device of an ECG sensor. ECG sensor 148 may receive electrical signals from electrodes, may amplify such signals and convert them into a visual representation, such as a waveform. ECG sensor 148 may include one or more lead wires. ECG sensor 148 may include a device configured to measure and/or interpret electrical activity of heart of subject 132 using electrodes and/or lead wires. In some embodiments, ECG sensor 148 may be configured to detect ECG datum 144 and/or transmit ECG datum 144 to computing device 116. In some embodiments, ECG sensor 148 may include a surface ECG sensor. In some embodiments, ECG sensor 148 may include an intracardiac ECG sensor.

Still referring to FIG. 1, in some embodiments, PFA data 128 may include image data. Such image data may include cardiac image data. Cardiac image data may be obtained by, in non-limiting examples, echocardiogram, cardiac computed tomography, nuclear cardiac stress test, single-photon emission computed tomography, cardiac positron emission tomography, coronary angiogram, cardiac MRI, and multi-gated acquisition scan.

Still referring to FIG. 1, in some embodiments, apparatus 100 generates PFA durability datum 152 as a function of PFA data 128 using a trained PFA durability machine learning model 156. As used in this disclosure, a "PFA durability machine learning model" is any machine-learning model, process, or algorithm that outputs a PFA durability datum. As used herein, a "PFA durability datum" is a representation of PFA durability, for example measurement, quantification, prediction, estimate, and/or probability of PFA durability. As used herein, "PFA durability" is a tendency for tissue treated with pulsed field ablation to remain affected by the pulse field ablation, e.g., stay dead. PFA durability machine learning model 156 may be trained using a supervised learning algorithm. PFA durability machine learning model 156 may be trained on training data 160 including example PFA data 164, associated with example PFA outcomes 168. As used in this disclosure, a "PFA outcome" is used to describe both (1) physiological results of PFA procedures; and (2) representation of these results. PFA outcomes may be represented according to medical device measurements (e.g., ECG), doctor notes, patient accounts, and the like. In some cases, example PFA data 164 may include example PFA device parameters 164. Once PFA durability machine learning model 156 is trained, it may be used to determine PFA durability datum 152. Apparatus 100 may input PFA data 128 into PFA durability machine learning model 156, and apparatus 100 may receive PFA durability datum 152 from the model. In a non-limiting example, PFA durability machine learning model 156 may be trained on a training dataset including example PFA device parameters associated with example PFA outcomes 168, and PFA durability machine learning model 156 may accept as an input PFA device parameter 136. In another non-limiting example, PFA durability machine learning model 156 may be trained on a training dataset including example ECG data associated with example PFA outcomes 168, and PFA durability machine learning model 156 may accept as an input ECG datum 144. In some embodiments, training dataset for PFA durability machine-learning model may include ECG data and/or electrogram (EGM) data correlated to PFA outcomes. In some embodiments, training dataset for PFA may include in-procedure ECG data and/or in-procedure electrogram data correlated to PFA outcomes. For the purposes of this disclosure, "in-procedure ECG data" refers to data that is collected using an ECG during an ablation procedure. For the purposes of this disclosure, "in-procedure EGM data" refers to data that is collected using an EGM during an ablation procedure. In some embodiments, PFA durability machine learning model 156 may include a fused classifier ensemble machine learning model. For example, the output of one or more classifiers may be used as inputs in another machine learning step. Such a system may use gradient boosting, such as, in a non-limiting example, Cat-Boost. In some embodiments, PFA durability machine learning model 156 may include a 1 dimensional convolutional neural network, such as, in a non-limiting example, U-Net.

In some embodiments a 1 dimensional convolutional neural network may be used to interpret intracardiac voltage and/or surface voltage input data. In some embodiments, PFA durability machine learning model 156 may include a 2 dimensional convolutional neural network. In a non-limiting example, a 2 dimensional convolutional neural network may be used to interpret CT scans and/or MRI scans to create classifications between geometric surfaces which may be predictive of Afib recurrence.

Still referring to FIG. 1, in some embodiments, PFA durability datum 152 may include a likelihood and/or probability that a lesion is predicted to be durable. In some embodiments, a probability that a lesion is predicted to be durable is expressed as a number from 0 to 1. In some embodiments, a probability that a lesion is predicted to be durable is expressed as a percentage. In some embodiments, PFA durability datum 152 may include a length of time over which a lesion is predicted to be durable. In some embodiments, PFA durability datum 152 may include a Boolean variable representing whether or not a lesion is predicted to be durable. In some embodiments, PFA durability datum 152 represented on a continuum may be mapped to one or more fuzzy sets representing values of linguistic variables.

Still referring to FIG. 1, in some embodiments, example PFA outcomes 168 may be determined from patient medical records. Example PFA outcomes 168 may include diagnoses, such as whether AFib recurred and/or resolved, and ECG data, such as ECG data of a form described above. In some embodiments, example PFA outcomes 168 may be determined from image data, such as image data generated using, in non-limiting examples, echocardiogram, cardiac computed tomography, nuclear cardiac stress test, single-photon emission computed tomography, cardiac positron emission tomography, coronary angiogram, cardiac MRI, and multigated acquisition scan. In some embodiments, example PFA outcomes 168 may be determined using intracardiac echocardiography (ICE). In some cases, example PFA outcomes 168 may include a date of recurrence of AFib and/or a date of reperformed ablation. In some embodiments, such dates may be measured in absolute terms and/or in terms relative to a date of a PFA procedure. In some embodiments, PFA outcome data may include an AFib burden. As used herein, an "AFib burden data" is a representation of AFib experienced by a subject, for example quantity of Afib, quality of Afib, or both. In some embodiments, low AFib burden may correlate with positive example PFA outcomes as, in some cases, minor occasional AFib may not warrant a second cardiac ablation, for example. In some embodiments, example PFA data 164 may include historical PFA data in a form described above and/or gathered as described above with respect to PFA data 128. In some embodiments, example PFA outcomes 168 may be determined based on medical data of subjects captured after such subjects undergo PFA. In a non-limiting example, example PFA outcomes 168 may include historical post-PFA procedure ECG data. As used in this disclosure, "post-PFA procedure ECG data" is a representation of an any electrocardiogram-type of measurement taken on a subject, at any time, after a pulse field ablation procedure. Additional detail with respect to timing of data gathering is provided below. In some embodiments, example PFA outcomes 168 may be categorical, such as positive or negative outcome. In some embodiments, example PFA outcomes 168 may have a numerical value, such as a value within a range where values on one end of the range indicate positive outcomes and values on the other end of the range indicate negative outcomes.

Still referring to FIG. 1, in some embodiments, training data 160 may be stored in a data store 172 and/or memory 108. Data store 172 may be implemented, without limitation, as a relational database, a key-value retrieval database such as a NOSQL database, or any other format or structure for use as a database that a person skilled in the art would recognize as suitable upon review of the entirety of this disclosure. Data store 172 may alternatively or additionally be implemented using a distributed data storage protocol and/or data structure, such as a distributed hash table or the like. Data store 172 may include a plurality of data entries and/or records as described above. Data entries in a data store 172 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure. In some embodiments, PFA data 128 and/or follow up measurements of cardiac health of subject 132 may be stored in data store 172 and/or used as training data for further training of PFA durability machine learning model 156. In some embodiments, data store 172 may include an electronic health record database. In some embodiments, an electronic health record database may include health information such as example PFA data 164 and example PFA outcomes 168 from a plurality of subjects. In some embodiments, health information may be received in an anonymized state and/or may be anonymized by apparatus 100, such as by removing identifying information. Similarly, in some embodiments, computing device 116 may receive PFA data 128 from a data store, such as data store 172, rather than and/or in addition to receiving it from devices which measure such data. For example, PFA device 140 may transmit PFA device parameter 136 to a data store, and computing device 116 may subsequently receive such PFA device parameter 136 from such data store.

Still referring to FIG. 1, in some embodiments, training data 160 may include a plurality of instances of example subject demographic information, correlated to example PFA outcomes 168. PFA durability machine learning model 156 may accept as an input subject demographic information 176 and may output PFA durability datum 152 as a function of PFA data 128 and subject demographic information 176. As used herein, "subject demographic information" is a representation of demographic of a subject, for example, age of a subject, biological sex of a subject, ethnicity of a subject, or a combination thereof. In some embodiments, subject 132 may be classified to a particular cohort based on subject demographic information 176, and PFA durability datum 152 may be determined as a function of such cohort. In a non-limiting example, PFA durability machine learning model 156 may accept a cohort as an input. In another non-limiting example, PFA durability machine learning model 156 may be selected from a plurality of models as a function of a cohort. In a non-limiting example, a first PFA durability machine learning model may be trained on data of female subjects and may be applied to data of subjects in a female cohort, and a second PFA durability machine learning model may be trained on data of male subjects and may be applied to data of subjects in a male cohort.

Still referring to FIG. 1, in some embodiments, PFA data 128 may be captured before, concurrently with, and/or after a PFA procedure. In a non-limiting example, PFA data 128 may include ECG datum 144 captured before a PFA procedure. In some embodiments, a PFA datum may be captured more than 2 years before, 2 years before, 1 year before, 9 months before, 6 months before, 3 months before, 2 months before, 6 weeks before, 4 weeks before, 3 weeks before, 2 weeks before, 1 week before, 6 days before, 5 days before, 4 days before, 3 days before, 2 days before, 1 day before, the same day of, 1 day after, 2 days after, 3 days after, 4 days after, 5 days after, 6 days after, 1 week after, 2 weeks after, 3 weeks after, 4 weeks after, 6 weeks after, 2 months after, 3 months after, 6 months after, 9 months after, 1 year after, 2 years after, and/or more than 2 years after a PFA procedure. In some embodiments, PFA data 128 may be captured immediately before and/or immediately after a PFA procedure. Example PFA data 164 may be captured at such time frames with respect to a historical PFA procedure.

Still referring to FIG. 1, in some embodiments, PFA durability datum 152 may be determined before a PFA procedure. For example, PFA durability datum 152 may be determined as a function of a potential PFA device parameter and/or an ECG datum captured before a PFA procedure. In some embodiments, PFA device parameters used in a procedure may be optimized and/or modified based on PFA durability datum 152 produced from such data.

Still referring to FIG. 1, in some embodiments, example PFA outcomes 168 may include and/or be determined as a function of data captured concurrently with and/or after a PFA procedure. In a non-limiting example, example PFA outcomes 168 may include and/or be determined as a function of ECG data captured after a PFA procedure. In some embodiments, an example PFA outcome may be captured the same day of, 1 day after, 2 days after, 3 days after, 4 days after, 5 days after, 6 days after, 1 week after, 2 weeks after, 3 weeks after, 4 weeks after, 6 weeks after, 2 months after, 3 months after, 6 months after, 9 months after, 1 year after, 2 years after, and/or more than 2 years after a PFA procedure. In some embodiments, example PFA outcomes 168 may be captured immediately before and/or immediately after a PFA procedure.

Still referring to FIG. 1, in some embodiments, PFA durability machine learning model 156 may include a multimodal neural network. In some embodiments, a multimodal neural network may accept as multiple inputs of different modalities and may use such data to produce PFA durability datum 152. In a non-limiting example, PFA durability machine learning model 156 may accept ECG time series data, a PFA device parameter indicating a frequency of pulses of a PFA procedure, and subject demographic information 176 indicating ethnicity of a subject. In some embodiments, PFA durability machine learning model 156 may include a plurality of neural network fused together using a fused feature vector. For example, a first neural network may accept as an input data of a first modality such as ECG data, and a second neural network may accept as an input data of a second modality such as a PFA device parameter, and a fused feature vector may be used to merge outputs of the first and second neural networks. In some embodiments, a modality of a multi-modal neural network may include subject demographic information 176. Multimodal neural networks are described further herein with reference to FIG. 6.

Still referring to FIG. 1, in some embodiments, PFA durability machine learning model 156 may include a plurality of unimodal neural networks each trained to produce outputs in the form of predictions based on unimodal input data. Such outputs may be represented as linguistic variable values. Such a linguistic variable value may belong to one or more fuzzy sets. For example, fuzzy set membership of unimodal neural network outputs may be determined for each of a plurality of outputs of different modes. Such fuzzy sets may be associated with degrees of PFA durability, such as, in non-limiting examples, "highly durable," "moderately durable," or "not durable." In some embodiments, an inferencing rule may be applied to determine fuzzy set membership of a combined output based on fuzzy set membership of linguistic variables. In a non-limiting example, membership of a combined output in a "highly durable" fuzzy set may be determined based on a percentage membership of a first linguistic variable associated with a first mode in a "highly durable" fuzzy set and a percentage membership of a second linguistic variable associated with a second mode in a "moderately durable" fuzzy set. In some embodiments, PFA durability datum 152 may then be determined by comparison to a threshold or output using another defuzzification process. Each stage of such a process may be implemented using any type of machine learning model such as any type of neural network described herein. In some embodiments, parameters of one or more fuzzy sets may be tuned using machine learning. Fuzzy sets are described further herein with reference to FIG. 5.

Still referring to FIG. 1, in some embodiments, PFA durability machine learning model 156 may include a generative machine learning model. In some embodiments, a computing device may implement one or more aspects of "generative artificial intelligence," a type of artificial intelligence (AI) that uses machine learning algorithms to create, establish, or otherwise generate data such as, without limitation, PFA durability datum 152 and/or the like in any data structure as described herein (e.g., text, image, video, audio, among others) that is similar to one or more provided training examples. In an embodiment, machine learning module described herein may generate one or more generative machine learning models that are trained on one or more sets of training data 160. One or more generative machine learning models may be configured to generate new examples that are similar to the training data of the one or more generative machine learning models but are not exact replicas; for instance, and without limitation, data quality or attributes of the generated examples may bear a resemblance to the training data provided to one or more generative machine learning models, wherein the resemblance may pertain to underlying patterns, features, or structures found within the provided training data.

Still referring to FIG. 1, in some cases, generative machine learning models may include one or more generative models. A generative model may include a statistical model of the joint probability distribution $P(X, Y)$ on a given observable variable x, representing features or data that can be directly measured or observed and target variable y, representing the outcomes or labels that one or more generative models aims to predict or generate. For example, such variable x may include PFA data 128 and such variable y may include PFA durability datum 152.

Still referring to FIG. 1, in some cases, generative models may rely on Bayes theorem to find joint probability; for instance, and without limitation, Naïve Bayes classifiers may be employed by computing device to categorize input data such as, without limitation, PFA data 128 into different categories such as, without limitation, according to different demographics or different modalities.

Still referring to FIG. 1, in some embodiments, one or more generative machine learning models may include one or more Naïve Bayes classifiers generated, by computing device, using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P(A)=P(B), where P(A/B) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A Naïve Bayes algorithm may be generated by first transforming training data into a frequency table. Computing Device may then calculate a likelihood table by calculating probabilities of different data entries and classification labels. Computing device may utilize a Naïve Bayes equation to calculate a posterior probability for each class. A class containing the highest posterior probability is the outcome of prediction.

Still referring to FIG. 1, although Naïve Bayes classifier may be primarily known as a probabilistic classification algorithm; however, it may also be considered a generative model described herein due to its capability of modeling the joint probability distribution P(X, Y) over observable variables X and target variable Y. In an embodiment, Naïve Bayes classifier may be configured to make an assumption that the features X are conditionally independent given class label Y, allowing generative model to estimate the joint distribution as P(X, Y)=P(Y)πiP(Xi|Y), wherein P(Y) may be the prior probability of the class, and $P(X_i|Y)$ is the conditional probability of each feature given the class. One or more generative machine learning models containing Naïve Bayes classifiers may be trained on labeled training data, estimating conditional probabilities $P(X_i|Y)$ and prior probabilities P(Y) for each class; for instance, and without limitation, using techniques such as Maximum Likelihood Estimation (MLE). One or more generative machine learning models containing Naïve Bayes classifiers may select a class label y according to prior distribution P(Y), and for each feature $X_i$, sample at least a value according to conditional distribution $P(X_i|y)$. Sampled feature values may then be combined to form one or more new data instance with selected class label y. In a non-limiting example, one or more generative machine learning models may include one or more Naïve Bayes classifiers to generate new examples of PFA durability datum 152 based on classification of PFA data 128, wherein the models may be trained using training data containing a plurality of features e.g., features of PFA data 128, and/or the like as input correlated to a plurality of labeled classes as output.

Still referring to FIG. 1, in some cases, one or more generative machine learning models may include generative adversarial network (GAN). As used in this disclosure, a "generative adversarial network" is a type of artificial neural network with at least two sub models (e.g., neural networks), a generator, and a discriminator, that compete against each other in a process that ultimately results in the generator learning to generate new data samples, wherein the "generator" is a component of the GAN that learns to create hypothetical data by incorporating feedbacks from the "discriminator" configured to distinguish real data from the hypothetical data. In some cases, generator may learn to make discriminator classify its output as real. In an embodiment, discriminator may include a supervised machine learning model while generator may include an unsupervised machine learning model as described in further detail with reference to FIG. 2.

Still referring to FIG. 1, in some embodiments, discriminator may include one or more discriminative models, i.e., models of conditional probability P(Y|X=x) of target variable Y, given observed variable X. In an embodiment, discriminative models may learn boundaries between classes or labels in given training data. In a non-limiting example, discriminator may include one or more classifiers as described in further detail below with reference to FIG. 2 to distinguish between different categories such as real vs fake or correct vs incorrect, or states such as TRUE vs. FALSE within the context of generated data such as, without limitations, PFA durability datum 152, and/or the like. In some cases, computing device may implement one or more classification algorithms such as, without limitation, Support Vector Machines (SVM), Logistic Regression, Decision Trees, and/or the like to define decision boundaries.

Still referring to FIG. 1, in some embodiments, generator of GAN may be responsible for creating synthetic data that resembles real PFA durability datum 152. In some cases, GAN may be configured to receive PFA data 128 as input and generates corresponding PFA durability datum 152 containing information describing or evaluating the performance of one or more instances of PFA data 128. On the other hand, discriminator of GAN may evaluate the authenticity of the generated content by comparing it to real PFA durability datum 152, for example, discriminator may distinguish between genuine and generated content and providing feedback to generator to improve the model performance.

Still referring to FIG. 1, in some embodiments, one or more generative models may also include a variational autoencoder (VAE). As used in this disclosure, a "variational autoencoder" is an autoencoder (i.e., an artificial neural network architecture) whose encoding distribution is regularized during the model training process in order to ensure that its latent space includes desired properties allowing new data sample generation. In an embodiment, VAE may include a prior and noise distribution respectively, trained using expectation-maximization meta-algorithms such as, without limitation, probabilistic PCA, sparse coding, among others. In a non-limiting example, VEA may use a neural network as an amortized approach to jointly optimize across input data and output a plurality of parameters for corresponding variational distribution as it maps from a known input space to a low-dimensional latent space. Additionally, or alternatively, VAE may include a second neural network, for example, and without limitation, a decoder, wherein the "decoder" is configured to map from the latent space to the input space.

Still referring to FIG. 1, in some embodiments, VAE may be used by computing device to model complex relationships between PFA data 128. In some cases, VAE may encode input data into a latent space, capturing PFA durability datum 152. Such encoding process may include learning one or more probabilistic mappings from observed PFA data 128 to a lower-dimensional latent representation. Latent representation may then be decoded back into the original data space, therefore reconstructing the PFA data 128. In some cases, such decoding process may allow VAE to generate new examples or variations that are consistent with the learned distributions.

Still referring to FIG. 1, in some embodiments, one or more generative machine learning models may be trained on audio-visual data as described herein, wherein the audio-visual data may provide visual/acoustic information that generative machine learning models analyze to understand the dynamics of a heart. In other embodiments, training data may also include voice-over instructions, feedback, or the like. In some cases, such data may help generative machine learning models to learn appropriate language and tone for providing an audio natural language output.

Still referring to FIG. 1, in some embodiments, one or more generative machine learning models may utilize one or more predefined templates representing, for example, and without limitation, correct PFA durability datum 152. In a non-limiting example, one or more templates (i.e., predefined models or representations of correct and ideal PFA durability datum 152) may serve as benchmarks for comparing and evaluating PFA data 128.

Still referring to FIG. 1, computing device may configure generative machine learning models to analyze input data to one or more predefined templates, thereby allowing computing device to identify discrepancies or deviations from a desired form of PFA durability datum 152. In some cases, computing device may be configured to pinpoint specific errors in PFA data 128. In a non-limiting example, computing device may be configured to implement generative machine learning models to incorporate additional models to detect additional instances of PFA data 128. In some cases, errors may be classified into different categories or severity levels. In a non-limiting example, some errors may be considered minor, and generative machine learning model such as, without limitation, GAN may be configured to generate PFA durability datum 152 contain only slight adjustments while others may be more significant and demand more substantial corrections. In some embodiments, computing device may be configured to flag or highlight an error in input data and computing device may edit PFA data 128 using one or more generative machine learning models described herein. In some cases, one or more generative machine learning models may be configured to generate and output indicators such as, without limitation, visual indicator, audio indicator, and/or any other indicators as described above. Such indicators may be used to signal the detected error described herein.

Still referring to FIG. 1, in some cases, computing device may be configured to identify, and rank detected common deficiencies across a plurality of data sources; for instance, and without limitation, one or more machine learning models may classify errors in a specific order such as by ranking deficiencies in a descending order of commonality. Such ranking process may enable a prioritization of most prevalent issues, allowing instructors or computing device to address the issue.

Still referring to FIG. 1, in some cases, one or more generative machine learning models may also be applied by computing device to edit, modify, or otherwise manipulate existing data or data structures. In an embodiment, output of training data used to train one or more generative machine learning models such as GAN as described herein may include training data that linguistically or visually demonstrate modified PFA data 128. In some cases, PFA durability datum 152 may be synchronized with PFA data 128. In some cases, such PFA durability datum 152 may be integrated with the PFA data 128, offering a user a multisensory instructional experience.

Still referring to FIG. 1, computing device may be configured to continuously monitor PFA data 128. In an embodiment, computing device may configure discriminator to provide ongoing feedback and further corrections as needed to subsequent input data. In some cases, one or more sensors such as, without limitation, wearable device, motion sensor, or other sensors or devices described herein may provide additional PFA data 128 that may be used as subsequent input data or training data for one or more generative machine learning models described herein. An iterative feedback loop may be created as computing device continuously receive real-time data, identify errors as a function of real-time data, delivering corrections based on the identified errors, and monitoring a response on the delivered corrections. In an embodiment, computing device may be configured to retrain one or more generative machine learning models based on a response or update training data of one or more generative machine learning models by integrating a response into the original training data. In such embodiment, iterative feedback loop may allow machine learning module to adapt to a user's needs, enabling one or more generative machine learning models described herein to learn and update based on a response and generated feedback.

Still referring to FIG. 1, other exemplary embodiments of generative machine learning models may include, without limitation, long short-term memory networks (LSTMs), (generative pre-trained) transformer (GPT) models, mixture density networks (MDN), and/or the like.

Still referring to FIG. 1, in a further non-limiting embodiment, machine learning module may be further configured to generate a multi-model neural network that combines various neural network architectures described herein. In a non-limiting example, multi-model neural network may combine LSTM for time-series analysis with GPT models for natural language processing. Such fusion may be applied by computing device to generate PFA durability datum 152. In some cases, multi-model neural network may also include a hierarchical multi-model neural network, wherein the hierarchical multi-model neural network may involve a plurality of layers of integration; for instance, and without limitation, different models may be combined at various stages of the network. Convolutional neural network (CNN) may be used for image feature extraction, followed by LSTMs for sequential pattern recognition, and a MDN at the end for probabilistic modeling. Other exemplary embodiments of multi-model neural network may include, without limitation, ensemble-based multi-model neural network, cross-modal fusion, adaptive multi-model network, among others.

Still referring to FIG. 1, in some embodiments, PFA durability machine learning model 156 may include a language model such as an LLM. A language model may be used to process PFA data 128 such as physician notes of health of a subject, or other data in the form of text. For example, a language model may be used to produce an input for a further machine learning model which may produce PFA durability datum 152. As used herein, a "language model" is a program capable of interpreting natural language, generating natural language, or both. In some embodiments, a language model may be configured to interpret the output of an automatic speech recognition function and/or an OCR function. A language model may include a neural network. A language model may be trained using a dataset that includes natural language.

Still referring to FIG. 1, in some embodiments, a language model may be configured to extract one or more words from a document. One or more words may include, without limitation, strings of one or more characters, including without limitation any sequence or sequences of letters, numbers, punctuation, diacritic marks, engineering symbols, geometric dimensioning and tolerancing (GD & T) symbols, chemical symbols and formulas, spaces, whitespace, and other symbols. Textual data may be parsed into tokens, which may include a simple word (sequence of letters separated by whitespace) or more generally a sequence of characters. As used herein, a "token," is a smaller, individual grouping of text from a larger source of text. Tokens may be broken up by word, pair of words, sentence, or other delimitations. Tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as chains, for example for use as a Markov chain or Hidden Markov Model.

Still referring to FIG. 1, generating language model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 1, processor 104 may determine one or more language elements in PFA data 128 by identifying and/or detecting associations between one or more language elements (including phonemes or phonological elements, morphemes or morphological elements, syntax or syntactic elements, semantics or semantic elements, and pragmatic elements) extracted from at least PFA data 128, including without limitation mathematical associations, between such words. Associations between language elements and relationships of such categories to other such term may include, without limitation, mathematical associations, including without limitation statistical correlations between any language element and any other language element and/or Language elements. Processor 104 may compare an input such as a sentence from PFA data 128 with a list of keywords or a dictionary to identify language elements. For example, processor 104 may identify whitespace and punctuation in a sentence and extract elements comprising a string of letters, numbers or characters occurring adjacent to the whitespace and punctuation. Processor 104 may then compare each of these with a list of keywords or a dictionary. Based on the determined keywords or meanings associated with each of the strings, processor 104 may determine an association between one or more of the extracted strings and a feature of a subject apparatus 100, such as an association between a string containing the word "insulin" and the subject having diabetes. Associations may take the form of statistical correlations and/or mathematical associations, which may include probabilistic formulas or relationships indicating, for instance, a likelihood that a given extracted word indicates a given category of semantic meaning. As a further example, statistical correlations and/or mathematical associations may include probabilistic formulas or relationships indicating a positive and/or negative association between at least an extracted word and/or a given semantic meaning; positive or negative indication may include an indication that a given document is or is not indicating a category semantic meaning. Whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory.

Still referring to FIG. 1, processor 104 may be configured to determine one or more language elements in PFA data 128 using machine learning. For example, processor 104 may generate the language processing model by any suitable method, including without limitation a natural language processing classification algorithm; language processing model may include a natural language process classification model that enumerates and/or derives statistical relationships between input terms and output terms. An algorithm to generate language processing model may include a stochastic gradient descent algorithm, which may include a method that iteratively optimizes an objective function, such as an objective function representing a statistical estimation of relationships between terms, including relationships between input language elements and output patterns or conversational styles in the form of a sum of relationships to be estimated. In an alternative or additional approach, sequential tokens may be modeled as chains, serving as the observations in a Hidden Markov Model (HMM). HMMs as used herein are statistical models with inference algorithms that that may be applied to the models. In such models, a hidden state to be estimated may include an association between an extracted word, phrase, and/or other semantic unit. There may be a finite number of categories to which an extracted word may pertain; an HMM inference algorithm, such as the forward-backward algorithm or the Viterbi algorithm, may be used to estimate the most likely discrete state given a word or sequence of words. Language processing module may combine two or more approaches. For instance, and without limitation, machine-learning program may use a combination of Naïve-Bayes (NB), Stochastic Gradient Descent (SGD), and parameter grid-searching classification techniques; the result may include a classification algorithm that returns ranked associations.

Still referring to FIG. 1, processor 104 may be configured to determine one or more language elements in PFA data 128 using machine learning by first creating or receiving language classification training data. Training data may include data containing correlations that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below.

Still referring to FIG. 1, language classification training data may be a training data set containing associations between language element inputs and associated language element outputs. Language element inputs and outputs may be categorized by communication form such as written language elements, spoken language elements, typed language elements, or language elements communicated in any suitable manner. Language elements may be categorized by component type, such as phonemes or phonological elements, morphemes or morphological elements, syntax or syntactic elements, semantics or semantic elements, and pragmatic elements. Associations may be made between similar communication types of language elements (e.g. associating one written language element with another written language element) or different language elements (e.g. associating a spoken language element with a written representation of the same language element). Associations may be identified between similar communication types of two different language elements, for example written input consisting of the syntactic element "that" may be associated with written phonemes/th/,/ă/, and/t/. Associations may be identified between different communication forms of different language elements. For example, the spoken form of the syntactic element "that" and the associated written phonemes above. Language classification training data may be created using a classifier such as a language classifier. An exemplary classifier may be created, instantiated, and/or run using processor 104, or another computing device. Language classification training data may create associations between any type of language element in any format and other type of language element in any format. Additionally, or alternatively, language classification training data may associate language element input data to a feature related to a subject, a feature of a medical procedure, and the like. For example, language classification training data may associate occurrences of the syntactic elements "procedure," and "normal," in a single sentence with the feature of a medical procedure having been performed without issue.

Still referring to FIG. 1, processor 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A)\div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A Naïve Bayes algorithm may be generated by first transforming training data into a frequency table. Processor 104 may then calculate a likelihood table by calculating probabilities of different data entries and classification labels. Processor 104 may utilize a Naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

Still referring to FIG. 1, processor 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

Still referring to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a $$\text{Pythagorean norm: } l = \sqrt{\sum_{i=0}^{n} a_i^2},$$

where $a_i$ is attribute number i of the vector.

Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Still referring to FIG. 1, language processing module may use a corpus of documents to generate associations between language elements in a language processing module, and a diagnostic engine may then use such associations to analyze words extracted from one or more documents and determine that the one or more documents indicate significance of a category. In an embodiment, a computing device may perform this analysis using a selected set of significant documents, such as documents identified by one or more experts as representing good information; experts may identify or enter such documents via graphical user interface, or may communicate identities of significant documents according to any other suitable method of electronic communication, or by providing such identity to other persons who may enter such identifications into a computing device. Documents may be entered into a computing device by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, diagnostic engine may automatically obtain the document using such an identifier, for instance by submitting a request to a database or compendium of documents such as JSTOR as provided by Ithaka Harbors, Inc. of New York.

Still referring to FIG. 1, a machine learning model described herein may include a large language model (LLM). A "large language model," as used herein, is a deep learning data structure that can recognize, summarize, translate, predict and/or generate text and other content based on knowledge gained from massive datasets. Large language models may be trained on large sets of data. Training sets may be drawn from diverse sets of data such as, as non-limiting examples, novels, blog posts, articles, emails, unstructured data, electronic records, and the like. In some embodiments, training sets may include a variety of subject matters, such as, as nonlimiting examples, medical report documents, electronic health records, entity documents, business documents, inventory documentation, emails, user communications, advertising documents, newspaper articles, and the like. In some embodiments, training sets of an LLM may include information from one or more public or private databases. As a non-limiting example, training sets may include databases associated with an entity. In some embodiments, training sets may include portions of documents associated with electronic records correlated to examples of outputs. In an embodiment, an LLM may include one or more architectures based on capability requirements of an LLM. Exemplary architectures may include, without limitation, GPT (Generative Pretrained Transformer), BERT (Bidirectional Encoder Representations from Transformers), T5 (Text-To-Text Transfer Transformer), and the like. Architecture choice may depend on a needed capability such generative, contextual, or other specific capabilities.

With continued reference to FIG. 1, in some embodiments, an LLM may be generally trained. As used in this disclosure, a "generally trained" LLM is an LLM that is trained on a general training set comprising a variety of subject matters, data sets, and fields. In some embodiments, an LLM may be initially generally trained. Additionally, or alternatively, an LLM may be specifically trained. As used in this disclosure, a "specifically trained" LLM is an LLM that is trained on a specific training set, wherein the specific training set includes data including specific correlations for the LLM to learn. As a non-limiting example, an LLM may be generally trained on a general training set, then specifically trained on a specific training set. In an embodiment, specific training of an LLM may be performed using a supervised machine learning process. In some embodiments, generally training an LLM may be performed using an unsupervised machine learning process. As a non-limiting example, specific training set may include information from a database. As a non-limiting example, specific training set may include text related to the users such as user specific data for electronic records correlated to examples of outputs. In an embodiment, training one or more machine learning models may include setting the parameters of the one or more models (weights and biases) either randomly or using a pretrained model. Generally training one or more machine learning models on a large corpus of text data can provide a starting point for fine-tuning on a specific task. A model such as an LLM may learn by adjusting its parameters during the training process to minimize a defined loss function, which measures the difference between predicted outputs and ground truth. Once a model has been generally trained, the model may then be specifically trained to fine-tune the pretrained model on task-specific data to adapt it to the target task. Fine-tuning may involve training a model with task-specific training data, adjusting the model's weights to optimize performance for the particular task. In some cases, this may include optimizing the model's performance by fine-tuning hyperparameters such as learning rate, batch size, and regularization. Hyperparameter tuning may help in achieving the best performance and convergence during training. In an embodiment, fine-tuning a pretrained model such as an LLM may include fine-tuning the pretrained model using Low-Rank Adaptation (LoRA). As used in this disclosure, "Low-Rank Adaptation" is a training technique for large language models that modifies a subset of parameters in the model. Low-Rank Adaptation may be configured to make the training process more computationally efficient by avoiding a need to train an entire model from scratch. In an exemplary embodiment, a subset of parameters that are updated may include parameters that are associated with a specific task or domain.

With continued reference to FIG. 1, in some embodiments an LLM may include and/or be produced using Generative Pretrained Transformer (GPT), GPT-2, GPT-3, GPT-4, and the like. GPT, GPT-2, GPT-3, GPT-3.5, and GPT-4 are products of Open AI Inc., of San Francisco, CA. An LLM may include a text prediction based algorithm configured to receive an article and apply a probability distribution to the words already typed in a sentence to work out the most likely word to come next in augmented articles. For example, if some words that have already been typed are "Nice to meet", then it may be highly likely that the word "you" will come next. An LLM may output such predictions by ranking words by likelihood or a prompt parameter. For the example given above, an LLM may score "you" as the most likely, "your" as the next most likely, "his" or "her" next, and the like. An LLM may include an encoder component and a decoder component.

Still referring to FIG. 1, an LLM may include a transformer architecture. In some embodiments, encoder component of an LLM may include transformer architecture. A "transformer architecture," for the purposes of this disclosure is a neural network architecture that uses self-attention and positional encoding. Transformer architecture may be designed to process sequential input data, such as natural language, with applications towards tasks such as translation and text summarization. Transformer architecture may process the entire input all at once. "Positional encoding," for the purposes of this disclosure, refers to a data processing technique that encodes the location or position of an entity in a sequence. In some embodiments, each position in the sequence may be assigned a unique representation. In some embodiments, positional encoding may include mapping each position in the sequence to a position vector. In some embodiments, trigonometric functions, such as sine and cosine, may be used to determine the values in the position vector. In some embodiments, position vectors for a plurality of positions in a sequence may be assembled into a position matrix, wherein each row of position matrix may represent a position in the sequence.

With continued reference to FIG. 1, an LLM and/or transformer architecture may include an attention mechanism. An "attention mechanism," as used herein, is a part of a neural architecture that enables a system to dynamically quantify the relevant features of the input data. In the case of natural language processing, input data may be a sequence of textual elements. It may be applied directly to the raw input or to its higher-level representation.

With continued reference to FIG. 1, attention mechanism may represent an improvement over a limitation of an encoder-decoder model. An encoder-decider model encodes an input sequence to one fixed length vector from which the output is decoded at each time step. This issue may be seen as a problem when decoding long sequences because it may make it difficult for the neural network to cope with long sentences, such as those that are longer than the sentences in the training corpus. Applying an attention mechanism, an LLM may predict the next word by searching for a set of positions in a source sentence where the most relevant information is concentrated. An LLM may then predict the next word based on context vectors associated with these source positions and all the previously generated target words, such as textual data of a dictionary correlated to a prompt in a training data set. A "context vector," as used herein, are fixed-length vector representations useful for document retrieval and word sense disambiguation.

Still referring to FIG. 1, attention mechanism may include, without limitation, generalized attention self-attention, multi-head attention, additive attention, global attention, and the like. In generalized attention, when a sequence of words or an image is fed to an LLM, it may verify each element of the input sequence and compare it against the output sequence. Each iteration may involve the mechanism's encoder capturing the input sequence and comparing it with each element of the decoder's sequence. From the comparison scores, the mechanism may then select the words or parts of the image that it needs to pay attention to. In self-attention, an LLM may pick up particular parts at different positions in the input sequence and over time compute an initial composition of the output sequence. In multi-head attention, an LLM may include a transformer model of an attention mechanism. Attention mechanisms, as described above, may provide context for any position in the input sequence. For example, if the input data is a natural language sentence, the transformer does not have to process one word at a time. In multi-head attention, computations by an LLM may be repeated over several iterations, each computation may form parallel layers known as attention heads. Each separate head may independently pass the input sequence and corresponding output sequence element through a separate head. A final attention score may be produced by combining attention scores at each head so that every nuance of the input sequence is taken into consideration. In additive attention (Bahdanau attention mechanism), an LLM may make use of attention alignment scores based on a number of factors. Alignment scores may be calculated at different points in a neural network, and/or at different stages represented by discrete neural networks. Source or input sequence words are correlated with target or output sequence words but not to an exact degree. This correlation may take into account all hidden states and the final alignment score is the summation of the matrix of alignment scores. In global attention (Luong mechanism), in situations where neural machine translations are required, an LLM may either attend to all source words or predict the target sentence, thereby attending to a smaller subset of words.

With continued reference to FIG. 1, multi-headed attention in encoder may apply a specific attention mechanism called self-attention. Self-attention allows models such as an LLM or components thereof to associate each word in the input, to other words. As a non-limiting example, an LLM may learn to associate the word "you", with "how" and "are". It's also possible that an LLM learns that words structured in this pattern are typically a question and to respond appropriately. In some embodiments, to achieve self-attention, input may be fed into three distinct fully connected neural network layers to create query, key, and value vectors. Query, key, and value vectors may be fed through a linear layer; then, the query and key vectors may be multiplied using dot product matrix multiplication in order to produce a score matrix. The score matrix may determine the amount of focus for a word should be put on other words (thus, each word may be a score that corresponds to other words in the time-step). The values in score matrix may be scaled down. As a non-limiting example, score matrix may be divided by the square root of the dimension of the query and key vectors. In some embodiments, the softmax of the scaled scores in score matrix may be taken. The output of this softmax function may be called the attention weights. Attention weights may be multiplied by your value vector to obtain an output vector. The output vector may then be fed through a final linear layer.

Still referencing FIG. 1, in order to use self-attention in a multi-headed attention computation, query, key, and value may be split into N vectors before applying self-attention. Each self-attention process may be called a "head." Each head may produce an output vector and each output vector from each head may be concatenated into a single vector. This single vector may then be fed through the final linear layer discussed above. In theory, each head can learn something different from the input, therefore giving the encoder model more representation power.

With continued reference to FIG. 1, encoder of transformer may include a residual connection. Residual connection may include adding the output from multi-headed attention to the positional input embedding. In some embodiments, the output from residual connection may go through a layer normalization. In some embodiments, the normalized residual output may be projected through a pointwise feed-forward network for further processing. The pointwise feed-forward network may include a couple of linear layers with a ReLU activation in between. The output may then be added to the input of the pointwise feed-forward network and further normalized.

Continuing to refer to FIG. 1, transformer architecture may include a decoder. Decoder may a multi-headed attention layer, a pointwise feed-forward layer, one or more residual connections, and layer normalization (particularly after each sub-layer), as discussed in more detail above. In some embodiments, decoder may include two multi-headed attention layers. In some embodiments, decoder may be autoregressive. For the purposes of this disclosure, "autoregressive" means that the decoder takes in a list of previous outputs as inputs along with encoder outputs containing attention information from the input.

With further reference to FIG. 1, in some embodiments, input to decoder may go through an embedding layer and positional encoding layer in order to obtain positional embeddings. Decoder may include a first multi-headed attention layer, wherein the first multi-headed attention layer may receive positional embeddings.

With continued reference to FIG. 1, first multi-headed attention layer may be configured to not condition to future tokens. As a non-limiting example, when computing attention scores on the word "am," decoder should not have access to the word "fine" in "I am fine," because that word is a future word that was generated after. The word "am" should only have access to itself and the words before it. In some embodiments, this may be accomplished by implementing a look-ahead mask. Look ahead mask is a matrix of the same dimensions as the scaled attention score matrix that is filled with "0s" and negative infinities. For example, the top right triangle portion of look-ahead mask may be filled with negative infinities. Look-ahead mask may be added to scaled attention score matrix to obtain a masked score matrix. Masked score matrix may include scaled attention scores in the lower-left triangle of the matrix and negative infinities in the upper-right triangle of the matrix. Then, when the softmax of this matrix is taken, the negative infinities will be zeroed out; this leaves zero attention scores for "future tokens."

Still referring to FIG. 1, second multi-headed attention layer may use encoder outputs as queries and keys and the outputs from the first multi-headed attention layer as values. This process matches the encoder's input to the decoder's input, allowing the decoder to decide which encoder input is relevant to put a focus on. The output from second multi-headed attention layer may be fed through a pointwise feedforward layer for further processing.

With continued reference to FIG. 1, the output of the pointwise feedforward layer may be fed through a final linear layer. This final linear layer may act as a classifier. This classifier may be as big as the number of classes that you have. For example, if you have 10,000 classes for 10,000 words, the output of that classifier will be of size 10,000. The output of this classifier may be fed into a softmax layer which may serve to produce probability scores between zero and one. The index may be taken of the highest probability score in order to determine a predicted word.

Still referring to FIG. 1, decoder may take this output and add it to the decoder inputs. Decoder may continue decoding until a token is predicted. Decoder may stop decoding once it predicts an end token.

Continuing to refer to FIG. 1, in some embodiment, decoder may be stacked N layers high, with each layer taking in inputs from the encoder and layers before it. Stacking layers may allow an LLM to learn to extract and focus on different combinations of attention from its attention heads.

With continued reference to FIG. 1, an LLM may receive an input. Input may include a string of one or more characters. Inputs may additionally include unstructured data. For example, input may include one or more words, a sentence, a paragraph, a thought, a query, and the like. A "query" for the purposes of the disclosure is a string of characters that poses a question. In some embodiments, input may be received from a user device. User device may be any computing device that is used by a user. As non-limiting examples, user device may include desktops, laptops, smartphones, tablets, and the like. In some embodiments, input may include any set of data associated with a subject and/or medical data of a subject.

With continued reference to FIG. 1, an LLM may generate at least one annotation as an output. At least one annotation may be any annotation as described herein. In some embodiments, an LLM may include multiple sets of transformer architecture as described above. Output may include a textual output. A "textual output," for the purposes of this disclosure is an output comprising a string of one or more characters. Textual output may include, for example, a plurality of annotations for unstructured data. In some embodiments, textual output may include a phrase or sentence identifying the status of a user query. In some embodiments, textual output may include a sentence or plurality of sentences describing a response to a user query. As a non-limiting example, this may include restrictions, timing, advice, dangers, benefits, and the like.

With continued reference to FIG. 1, in an embodiment, PFA durability machine learning model 156 may include a deep neural network (DNN). As used in this disclosure, a "deep neural network" is defined as a neural network with two or more hidden layers. Neural network is described in further detail below with reference to FIGS. 3 and 4. In a non-limiting example, PFA durability machine learning model 156 may include a convolutional neural network (CNN). Generation of PFA durability datum 152 may include training CNN using training data 160 and generating PFA durability datum 152 using trained CNN. A "convolutional neural network," for the purpose of this disclosure, is a neural network in which at least one hidden layer is a convolutional layer that convolves inputs to that layer with a subset of inputs known as a "kernel," along with one or more additional layers such as pooling layers, fully connected layers, and the like. In some cases, CNN may include, without limitation, a deep neural network (DNN) extension. Mathematical (or convolution) operations performed in the convolutional layer may include convolution of two or more functions, where the kernel may be applied to input data e.g., PFA data 128 through a sliding window approach. In some cases, convolution operations may enable processor 104 to detect local/global patterns, edges, textures, and any other features described herein within PFA data 128. Features may be passed through one or more activation functions, such as without limitation, Rectified Linear Unit (ReLU), to introduce non-linearities into the processing step of generation of PFA durability datum 152. Additionally, or alternatively, CNN may also include one or more pooling layers, wherein each pooling layer is configured to reduce the dimensionality of input data while preserving essential features within the input data. In a non-limiting example, CNN may include one or more pooling layer configured to reduce the dimensions of feature maps by applying downsampling, such as max-pooling or average pooling, to small, non-overlapping regions of one or more features.

Still referring to FIG. 1, CNN may further include one or more fully connected layers configured to combine features extracted by the convolutional and pooling layers as described above. In some cases, one or more fully connected layers may allow for higher-level pattern recognition. In a non-limiting example, one or more fully connected layers may connect every neuron (i.e., node) in its input to every neuron in its output, functioning as a traditional feedforward neural network layer. In some cases, one or more fully connected layers may be used at the end of CNN to perform high-level reasoning and produce the final output such as, without limitation, PFA durability datum 152. Further, each fully connected layer may be followed by one or more dropout layers configured to prevent overfitting, and one or more normalization layers to stabilize the learning process described herein.

With continued reference to FIG. 1, in an embodiment, training the PFA durability machine learning model 156 (i.e., CNN) may include selecting a suitable loss function to guide the training process. In a non-limiting example, a loss function that measures the difference between the predicted PFA durability datum 152 and the ground truth 3D structure e.g., example PFA outcomes may be used, such as, without limitation, mean squared error (MSE) or a custom loss function may be designed for one or more embodiments described herein. Additionally, or alternatively, optimization algorithms, such as stochastic gradient descent (SGD), may then be used to adjust the PFA durability machine learning model's parameters to minimize such loss. Additionally, CNN may be extended with additional deep learning techniques, such as recurrent neural networks (RNNs) or attention mechanism, to capture additional features and/or data relationships within input data. These extensions may further enhance the accuracy and robustness of generation of PFA durability datum 152.

Still referring to FIG. 1, in some embodiments, a datum described herein may be displayed to a user. For example, a datum may be displayed to subject 132 and/or a medical professional monitoring health of subject 132. A datum may be displayed to a user by user interface 120. In some embodiments, a visual element and/or a visual element data structure including and/or referring to a visual element may be determined as a function of a variable described herein and such visual element may be displayed to a user.

Still referring to FIG. 1, in some embodiments, a visual element data structure may include a visual element. As used herein, a "visual element" is a datum that is displayed visually to a user. In some embodiments, a visual element data structure may include a rule for displaying visual element. In some embodiments, a visual element data structure may be determined as a function of PFA durability datum 152. In some embodiments, a visual element data structure may be determined as a function of an item from the list consisting of subject demographic information 176, PFA data 128, and PFA durability datum 152. In a non-limiting example, a visual element data structure may be generated such that visual element describing or highlighting PFA durability datum 152 is displayed to a user. In another non-limiting example, a visual element may display data used to determine PFA durability datum 152.

Still referring to FIG. 1, in some embodiments, visual element may include one or more elements of text, images, shapes, charts, particle effects, interactable features, and the like. For example, a visual element may include an interactable feature allowing a user to input subject demographic information 176.

Still referring to FIG. 1, a visual element data structure may include rules governing if or when visual element is displayed. In a non-limiting example, a visual element data structure may include a rule causing a visual element describing PFA durability datum 152 to be displayed when a user selects PFA durability datum 152 using a graphical user interface (GUI).

Still referring to FIG. 1, a visual element data structure may include rules for presenting more than one visual element, or more than one visual element at a time. In an embodiment, about 1, 2, 3, 4, 5, 10, 20, or 50 visual elements are displayed simultaneously.

Still referring to FIG. 1, a visual element data structure rule may apply to a single visual element or datum, or to more than one visual element or datum. For example, a visual element data structure may rank visual elements and/or other data and/or apply numerical values to them, and a computing device may display a visual element as a function of such rankings and/or numerical values. A visual element data structure may apply rules based on a comparison between such a ranking or numerical value and a threshold.

Still referring to FIG. 1, in some embodiments, visual element may be interacted with. For example, visual element may include an interface, such as a button or menu. In some embodiments, visual element may be interacted with using a user device such as a smartphone.

Still referring to FIG. 1, in some embodiments, apparatus 100 may transmit visual element data structure to user device 124. In some embodiments, visual element data structure may configure user device 124 to display visual element. In some embodiments, visual element data structure may cause an event handler to be triggered in an application of user device 124 such as a web browser. In some embodiments, triggering of an event handler may cause a change in an application of user device 124 such as display of visual element.

Still referring to FIG. 1, in some embodiments, apparatus 100 may transmit visual element to a display. A display may communicate visual element to user. A display may include, for example, a smartphone screen, a computer screen, or a tablet screen. A display may be configured to provide a visual interface. A visual interface may include one or more virtual interactive elements such as, without limitation, buttons, menus, and the like. A display may include one or more physical interactive elements, such as buttons, a computer mouse, or a touchscreen, that allow user to input data into the display. Interactive elements may be configured to enable interaction between a user and a computing device. In some embodiments, a visual element data structure is determined as a function of data input by user into a display.

Still referring to FIG. 1, a variable and/or datum described herein may be represented as a data structure. In some embodiments, a data structure may include one or more functions and/or variables, as a class might in object-oriented programming. In some embodiments, a data structure may include data in the form of a Boolean, integer, float, string, date, and the like. In a non-limiting example, a subject demographic information data structure may include an int value representing age of a subject in years. In some embodiments, data in a data structure may be organized in a linked list, tree, array, matrix, tenser, and the like. In some embodiments, a data structure may include or be associated with one or more elements of metadata. A data structure may include one or more self-referencing data elements, which processor 104 may use in interpreting the data structure. In a non-limiting example, a data structure may include "<date>" and "</date>," tags, indicating that the content between the tags is a date.

Still referring to FIG. 1, a data structure may be stored in, for example, memory 108 or a database. Database may be implemented, without limitation, as a relational database, a key-value retrieval database such as a NOSQL database, or any other format or structure for use as a database that a person skilled in the art would recognize as suitable upon review of the entirety of this disclosure. Database may alternatively or additionally be implemented using a distributed data storage protocol and/or data structure, such as a distributed hash table or the like. Database may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

Still referring to FIG. 1, in some embodiments, a data structure may be read and/or manipulated by processor 104. In a non-limiting example, a ECG datum data structure may be read and input into PFA durability machine learning model 156.

Still referring to FIG. 1, in some embodiments, a data structure may be calibrated. In some embodiments, a data structure may be trained using a machine learning algorithm. In a non-limiting example, a data structure may include an array of data representing the biases of connections of a neural network. In this example, the neural network may be trained on a set of training data, and a back propagation algorithm may be used to modify the data in the array. Machine learning models and neural networks are described further herein.

Still referring to FIG. 1, in some embodiments, a data structure may include categorical data. In a non-limiting example, a data structure input into PFA durability machine learning model 156 may indicate that a subject has partial membership in a category associated with having a particular medical condition. In some embodiments, a data structure may include data that has partial membership in a category. In a non-limiting example, datum such as a datum of PFA data 128 may be a variable within the range [0:1], where its value represents the percentage membership of a subject in a category associated with having a particular medical condition such as a disease. Fuzzy sets and fuzzy inferencing systems are described further herein.

Figure 2:
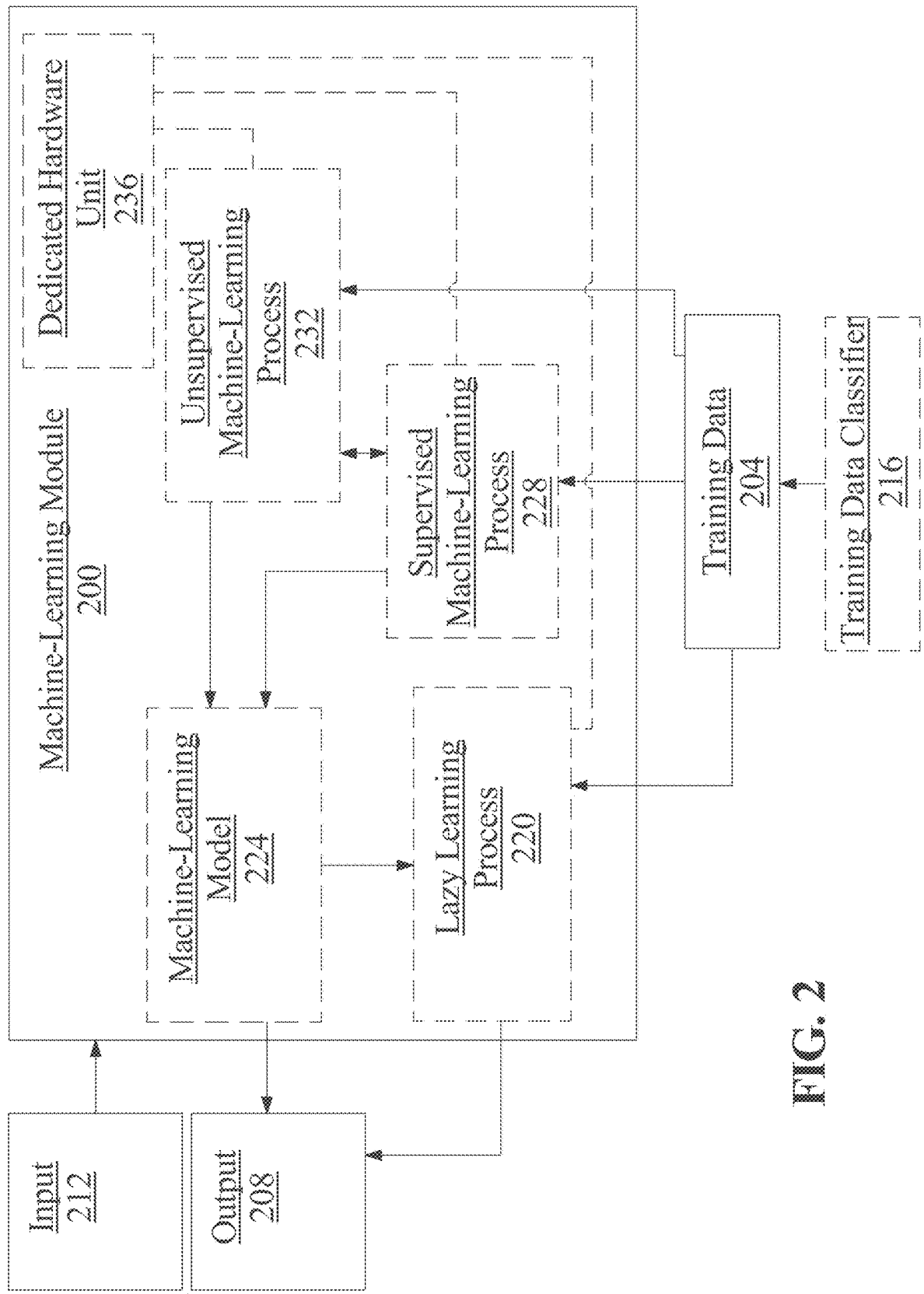
FIG. 2 is a block diagram of an exemplary embodiment of a machine learning model.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm instantiated in hardware or software logic, data structures, and/or functions that will be performed by a computing device/module to produce outputs 208 given data provided as inputs 212; this is in contrast to a non-machine learning software program where the commands to be executed are determined in advance by a user and written in a programming language.

Still referring to FIG. 2, "training data," or "training set," as used herein, is data that a machine-learning process may use to model relationships between two or more categories of data elements. For instance, and without limitation, training data 204 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail below. Training data 204 used by machine-learning module 200 may correlate any input data as described in this disclosure to any output data as described in this disclosure. As a non-limiting illustrative example, inputs may include PFA data 128 and outputs may include PFA durability datum 152.

Further referring to FIG. 2, training data may be filtered, sorted, and/or selected using one or more supervised and/or unsupervised machine-learning processes and/or models as described in further detail below; such models may include without limitation a training data classifier 216. Training data classifier 216 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 200 may generate a classifier using a classification algorithm, defined as a processes whereby a computing device and/or any module and/or component operating thereon derives a classifier from training data 204. Classification may be performed using, without limitation, linear classifiers such as without limitation logistic regression and/or Naïve Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of training data to particular demographic groups.

Still referring to FIG. 2, Computing device may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A) \div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A Naïve Bayes algorithm may be generated by first transforming training data into a frequency table. Computing device may then calculate a likelihood table by calculating probabilities of different data entries and classification labels. Computing device may utilize a Naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 2, Computing device may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 2, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute/as derived using a $$\text{Pythagorean norm: } l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 2, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 2, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 2, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 2, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 2, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 2, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 2, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 2, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $$X_{max}: X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation σ of a set or subset of values:

$$X_{new} = \frac{X - X_{mean}}{\sigma}.$$

Scaling may be performed using a median value of a a set or subset $X_{median}$ and/or interquartile range (IQR), which represents the difference between the 25$^{th}$ percentile value and the 50$^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 2, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements. Lazy learning may implement any suitable lazy learning algorithm, including without limitation a K-nearest neighbors algorithm, a lazy Naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 2, machine-learning processes as described in this disclosure may be used to generate machine-learning models 224. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include inputs as described above as inputs, outputs as described above as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

With further reference to FIG. 2, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 2, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 2, machine learning processes may include at least an unsupervised machine-learning processes 232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 232 may not require a response variable; unsupervised processes 232 may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include Naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 2, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry.

Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 2, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 2, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 2, one or more processes or algorithms described above may be performed by at least a dedicated hardware unit 236. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 236 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 236 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 236 to perform one or more operations described herein, such as evaluation of model and/or algorithm outputs, one-time or iterative updates to parameters, coefficients, weights, and/or biases, and/or any other operations such as vector and/or matrix operations as described in this disclosure.

With continued reference to FIG. 2, apparatus 100 may use user feedback to train the machine-learning models and/or classifiers described above. For example, classifier may be trained using past inputs and outputs of classifier. In some embodiments, if user feedback indicates that an output of classifier was "bad," then that output and the corresponding input may be removed from training data used to train classifier, and/or may be replaced with a value entered by, e.g., another user that represents an ideal output given the input the classifier originally received, permitting use in retraining, and adding to training data; in either case, classifier may be retrained with modified training data as described in further detail below. In some embodiments, training data of classifier may include user feedback.

With continued reference to FIG. 2, in some embodiments, an accuracy score may be calculated for classifier using user feedback. For the purposes of this disclosure, "accuracy score," is a numerical value concerning the accuracy of a machine-learning model. For example, a plurality of user feedback scores may be averaged to determine an accuracy score. In some embodiments, a cohort accuracy score may be determined for particular cohorts of persons. For example, user feedback for users belonging to a particular cohort of persons may be averaged together to determine the cohort accuracy score for that particular cohort of persons and used as described above. Accuracy score or another score as described above may indicate a degree of retraining needed for a machine-learning model such as a classifier; apparatus 100 may perform a larger number of retraining cycles for a higher number (or lower number, depending on a numerical interpretation used), and/or may collect more training data for such retraining, perform more training cycles, apply a more stringent convergence test such as a test requiring a lower mean squared error, and/or indicate to a user and/or operator that additional training data is needed.

Figure 3:
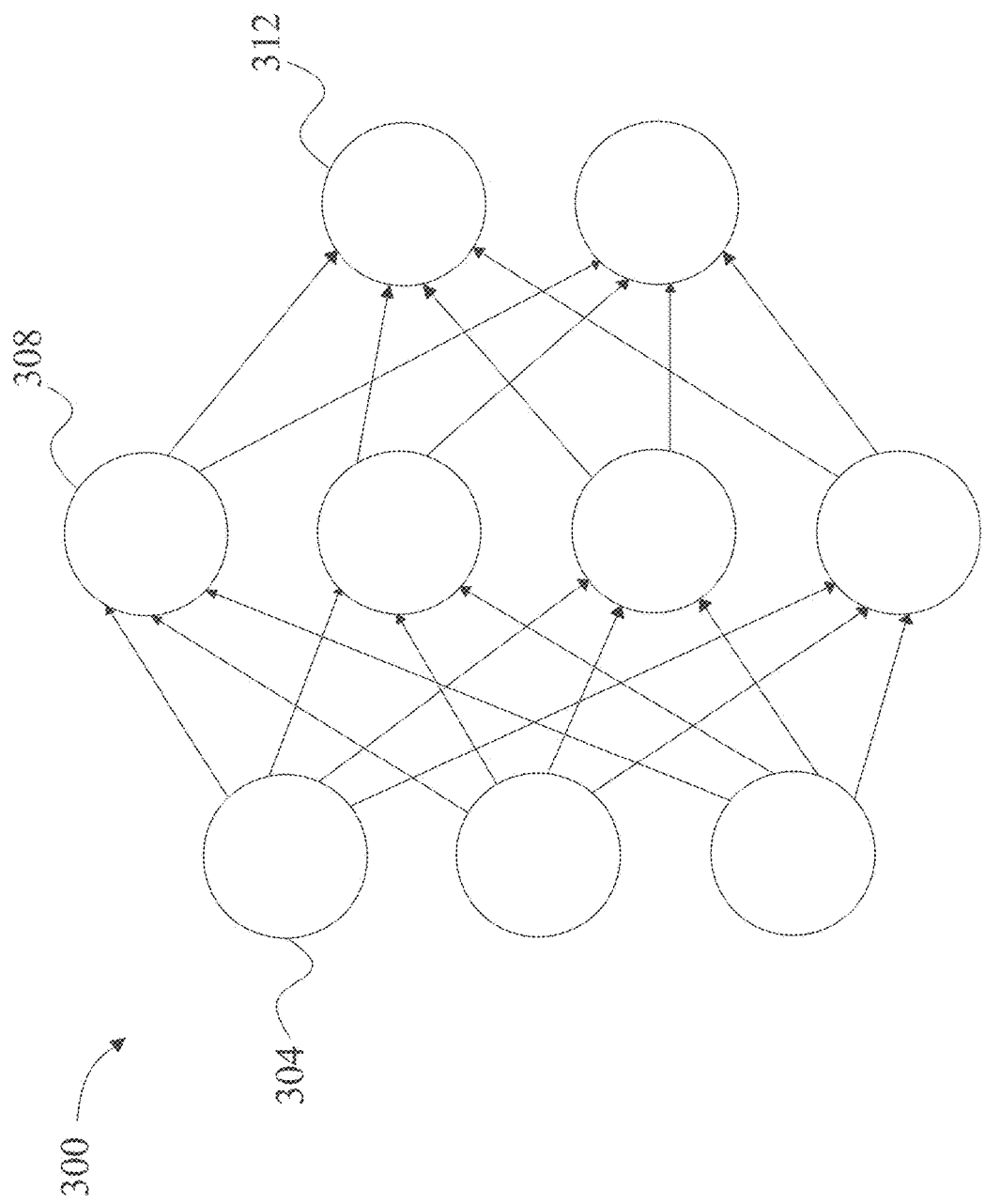
FIG. 3 is a schematic diagram of an exemplary embodiment of a neural network.

Referring now to FIG. 3, an exemplary embodiment of neural network 300 is illustrated. A neural network 300 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 304, one or more intermediate layers 308, and an output layer of nodes 312. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes.

Figure 4:
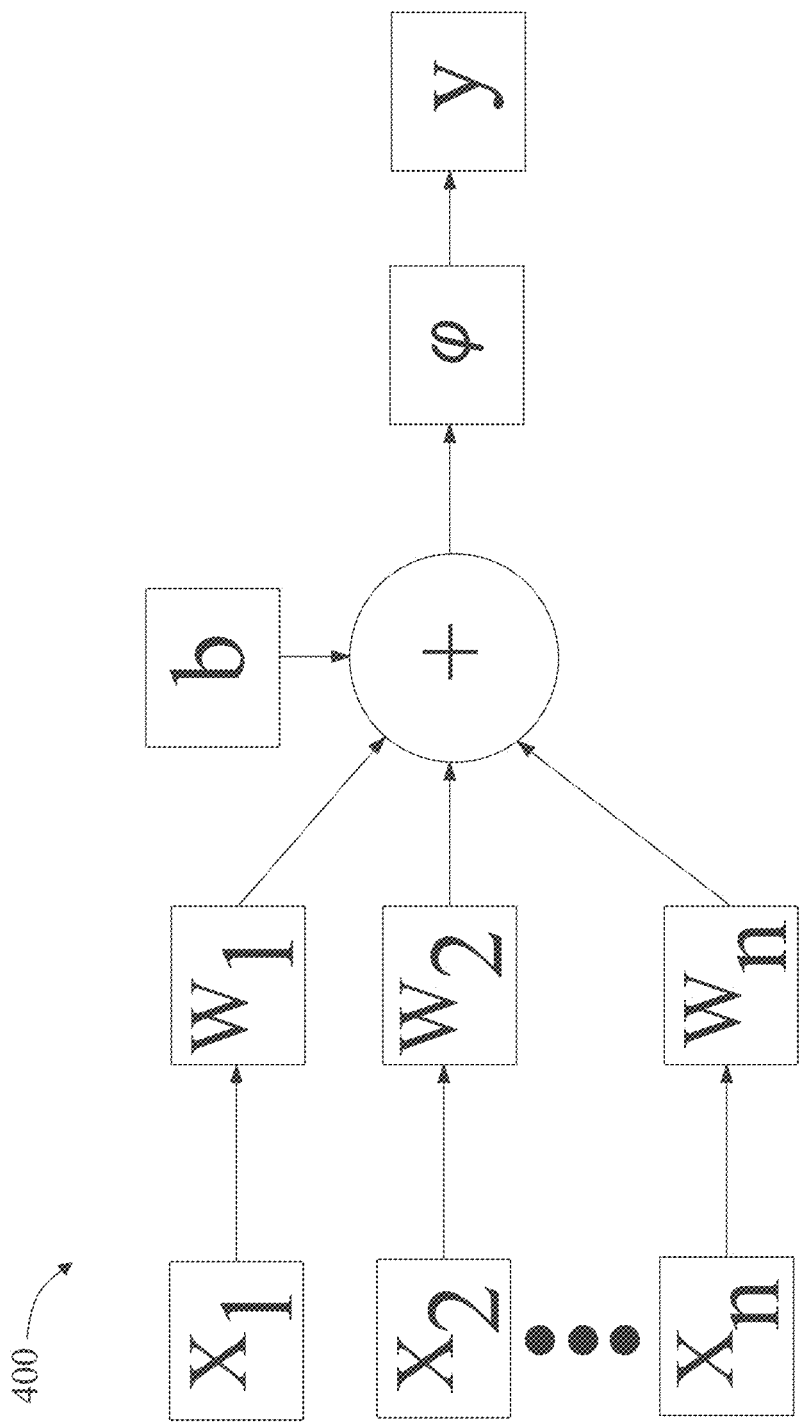
FIG. 4 is a schematic diagram of an exemplary embodiment of a neural network node.

Referring now to FIG. 4, an exemplary embodiment of a node 400 of a neural network is illustrated. A node may include, without limitation a plurality of inputs x; that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1-e^{-x}} \text{ given}$$

input x, a tanh (hyperbolic tangent) function, of the form $$\frac{e^x - e^{-x}}{e^x + e^{-x}},$$

a tanh derivative function such as $f(x)=\tanh^2(x)$, a rectified linear unit function such as $f(x)=\max(0, x)$, a "leaky" and/or "parametric" rectified linear unit function such as $f(x)=\max(ax, x)$ for some a, an exponential linear units function such as $$f(x) = \begin{cases} x \text{ for } x \geq 0 \\ \alpha(e^x - 1) \text{ for } x < 0 \end{cases}$$

for some value of a (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x)=x*\text{sigmoid}(x)$, a Gaussian error linear unit function such as $f(x)=a(1+\tanh(\sqrt{2/\pi}(x+bx^r)))$ for some values of a, b, and r, and/or a scaled exponential linear unit function such as $$f(x) = \lambda \begin{cases} \alpha(e^x - 1) \text{ for } x < 0 \\ x \text{ for } x \geq 0 \end{cases}.$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input x; may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 5:
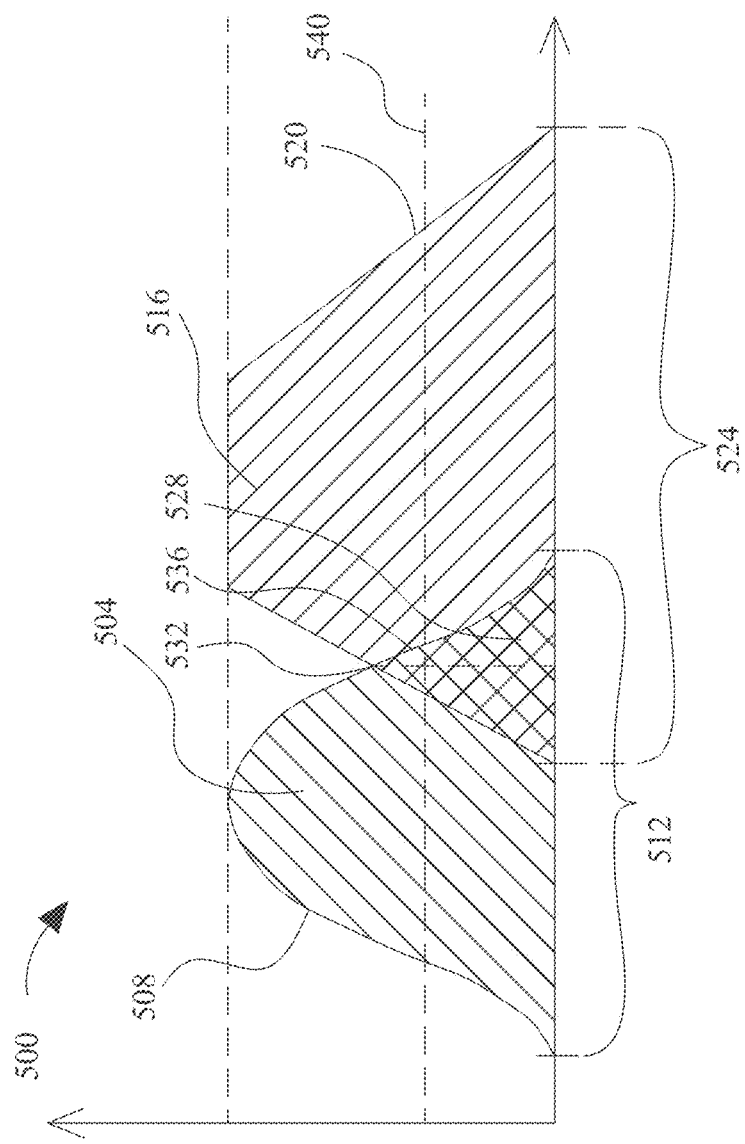
FIG. 5 is a schematic diagram of an exemplary embodiment of a fuzzy set inferencing system.

Referring to FIG. 5, an exemplary embodiment of fuzzy set comparison 500 is illustrated. A first fuzzy set 504 may be represented, without limitation, according to a first membership function 508 representing a probability that an input falling on a first range of values 512 is a member of the first fuzzy set 504, where the first membership function 508 has values on a range of probabilities such as without limitation the interval [0,1], and an area beneath the first membership function 508 may represent a set of values within first fuzzy set 504. Although first range of values 512 is illustrated for clarity in this exemplary depiction as a range on a single number line or axis, first range of values 512 may be defined on two or more dimensions, representing, for instance, a Cartesian product between a plurality of ranges, curves, axes, spaces, dimensions, or the like. First membership function 508 may include any suitable function mapping first range 512 to a probability interval, including without limitation a triangular function defined by two linear elements such as line segments or planes that intersect at or below the top of the probability interval. As a non-limiting example, triangular membership function may be defined as:

$$y(x, a, b, c) = \begin{cases} 0, \text{ for } x > c \text{ and } x < a \\ \frac{x-a}{b-a}, \text{ for } a \le x < b \\ \frac{c-x}{c-b}, \text{ if } b < x \le c \end{cases}$$

a trapezoidal membership function may be defined as:

$$y(x, a, b, c, d) = \max\left(\min\left(\frac{x-a}{b-a}, 1, \frac{d-x}{d-c}\right), 0\right)$$

a sigmoidal function may be defined as:

$$y(x, a, c) = \frac{1}{1 - e^{-a(x-c)}}$$

a Gaussian membership function may be defined as:

$$y(x, c, \sigma) = e^{-\frac{1}{2}\left(\frac{x-c}{\sigma}\right)^2}$$

and a bell membership function may be defined as:

$$y(x, a, b, c,) = \left[1 + \left|\frac{x-c}{a}\right|^{2b}\right]^{-1}$$

Persons skilled in the art, upon reviewing the entirety of this disclosure, will be aware of various alternative or additional membership functions that may be used consistently with this disclosure.

Still referring to FIG. 5, first fuzzy set 504 may represent any value or combination of values as described above, including output from one or more machine-learning models, unimodal predictions, and a predetermined class, such as without limitation of PFA durability. A second fuzzy set 516, which may represent any value which may be represented by first fuzzy set 504, may be defined by a second membership function 520 on a second range 524; second range 524 may be identical and/or overlap with first range 512 and/or may be combined with first range via Cartesian product or the like to generate a mapping permitting evaluation overlap of first fuzzy set 504 and second fuzzy set 516. Where first fuzzy set 504 and second fuzzy set 516 have a region 528 that overlaps, first membership function 508 and second membership function 520 may intersect at a point 532 representing a probability, as defined on probability interval, of a match between first fuzzy set 504 and second fuzzy set 516. Alternatively or additionally, a single value of first and/or second fuzzy set may be located at a locus 536 on first range 512 and/or second range 524, where a probability of membership may be taken by evaluation of first membership function 508 and/or second membership function 520 at that range point. A probability at 528 and/or 532 may be compared to a threshold 540 to determine whether a positive match is indicated. Threshold 540 may, in a non-limiting example, represent a degree of match between first fuzzy set 504 and second fuzzy set 516, and/or single values therein with each other or with either set, which is sufficient for purposes of the matching process; for instance, threshold may indicate a sufficient degree of overlap between an output from one or more machine-learning models and/or unimodal predictions and a predetermined class, such as without limitation PFA durability categorization, for combination to occur as described above. Alternatively, or additionally, each threshold may be tuned by a machine-learning and/or statistical process, for instance and without limitation as described in further detail below.

Further referring to FIG. 5, in an embodiment, a degree of match between fuzzy sets may be used to classify an unimodal predictions with PFA durability. For instance, if a PFA durability has a fuzzy set matching unimodal predictions fuzzy set by having a degree of overlap exceeding a threshold, processor 104 may classify the unimodal predictions as belonging to the PFA durability categorization. Where multiple fuzzy matches are performed, degrees of match for each respective fuzzy set may be computed and aggregated through, for instance, addition, averaging, or the like, to determine an overall degree of match.

Still referring to FIG. 5, in an embodiment, an unimodal predictions may be compared to multiple PFA durability categorization fuzzy sets. For instance, unimodal predictions may be represented by a fuzzy set that is compared to each of the multiple PFA durability categorization fuzzy sets; and a degree of overlap exceeding a threshold between the unimodal predictions fuzzy set and any of the multiple PFA durability categorization fuzzy sets may cause processor 104 to classify the unimodal predictions as belonging to PFA durability categorization. For instance, in one embodiment there may be two PFA durability categorization fuzzy sets, representing respectively high durability and low durability. First PFA durability categorization may have a first fuzzy set; Second PFA durability categorization may have a second fuzzy set; and unimodal predictions may have an unimodal predictions fuzzy set. processor 104, for example, may compare an unimodal predictions fuzzy set with each of PFA durability categorization fuzzy set and in PFA durability categorization fuzzy set, as described above, and classify a unimodal predictions to either, both, or neither of PFA durability categorization or in PFA durability categorization. Machine-learning methods as described throughout may, in a non-limiting example, generate coefficients used in fuzzy set equations as described above, such as without limitation x, c, and σ of a Gaussian set as described above, as outputs of machine-learning methods. Likewise, unimodal predictions may be used indirectly to determine a fuzzy set, as unimodal predictions fuzzy set may be derived from outputs of one or more machine-learning models that take the unimodal predictions directly or indirectly as inputs.

Still referring to FIG. 5, a computing device may use a logic comparison program, such as, but not limited to, a fuzzy logic model to determine a PFA durability response.

An PFA durability response may include, but is not limited to high durability, moderate durability, low durability, and the like; each such PFA durability response may be represented as a value for a linguistic variable representing PFA durability response or in other words a fuzzy set as described above that corresponds to a degree of durability as calculated using any statistical, machine-learning, or other method that may occur to a person skilled in the art upon reviewing the entirety of this disclosure. In other words, a given element of unimodal predictions may have a first non-zero value for membership in a first linguistic variable value such as high durability and a second non-zero value for membership in a second linguistic variable value such as low durability. In some embodiments, determining a PFA durability categorization may include using a linear regression model. A linear regression model may include a machine learning model. A linear regression model may be configured to map data of unimodal predictions, such as degree of . . . to one or more PFA durability parameters. A linear regression model may be trained using a machine learning process. A linear regression model may map statistics such as, but not limited to, quality of unimodal predictions . . . In some embodiments, determining an PFA durability of unimodal predictions may include using a PFA durability classification model. An PFA durability classification model may be configured to input collected data and cluster data to a centroid based on, but not limited to, frequency of appearance, linguistic indicators of quality, and the like. Centroids may include scores assigned to them such that quality of . . . of unimodal predictions may each be assigned a score. In some embodiments PFA durability classification model may include a K-means clustering model. In some embodiments, PFA durability classification model may include a particle swarm optimization model. In some embodiments, determining the PFA durability of an unimodal predictions may include using a fuzzy inference engine. A fuzzy inference engine may be configured to map one or more unimodal predictions data elements using fuzzy logic. In some embodiments, unimodal predictions may be arranged by a logic comparison program into PFA durability arrangement. An "PFA durability arrangement" as used in this disclosure is any grouping of objects and/or data based on skill level and/or output score. This step may be implemented as described herein with respect to other figures. Membership function coefficients and/or constants as described above may be tuned according to classification and/or clustering algorithms. For instance, and without limitation, a clustering algorithm may determine a Gaussian or other distribution of questions about a centroid corresponding to a given durability level, and an iterative or other method may be used to find a membership function, for any membership function type as described above, that minimizes an average error from the statistically determined distribution, such that, for instance, a triangular or Gaussian membership function about a centroid representing a center of the distribution that most closely matches the distribution. Error functions to be minimized, and/or methods of minimization, may be performed without limitation according to any error function and/or error function minimization process and/or method as described in this disclosure.

Further referring to FIG. 5, an inference engine may be implemented according to input and/or output membership functions and/or linguistic variables. For instance, a first linguistic variable may represent a first measurable value pertaining to unimodal predictions, such as a degree of durability of an element, while a second membership function may indicate a degree of in PFA durability of a subject thereof, or another measurable value pertaining to unimodal predictions. Continuing the example, an output linguistic variable may represent, without limitation, a score value. An inference engine may combine rules, such as: "if a first unimodal prediction is 'high durability' and a second unimodal prediction is 'moderate durability', the multimodal output is 'high durability.'—the degree to which a given input function membership matches a given rule may be determined by a triangular norm or "T-norm" of the rule or output membership function with the input membership function, such as min (a, b), product of a and b, drastic product of a and b, Hamacher product of a and b, or the like, satisfying the rules of commutativity (T(a, b)=T(b, a)), monotonicity: (T(a, b)≤T(c, d) if a≤c and b≤d), (associativity: T(a, T(b, c))=T(T(a, b), c)), and the requirement that the number 1 acts as an identity element. Combinations of rules ("and" or "or" combination of rule membership determinations) may be performed using any T-conorm, as represented by an inverted T symbol or "⊥," such as max(a, b), probabilistic sum of a and b (a+b−a*b), bounded sum, and/or drastic T-conorm; any T-conorm may be used that satisfies the properties of commutativity: ⊥(a, b)=⊥(b, a), monotonicity: ⊥(a, b)≤⊥(c, d) if a≤c and b≤d, associativity: ⊥(a, ⊥(b, c))=⊥(⊥(a, b), c), and identity element of 0. Alternatively or additionally T-conorm may be approximated by sum, as in a "product-sum" inference engine in which T-norm is product and T-conorm is sum. A final output score or other fuzzy inference output may be determined from an output membership function as described above using any suitable defuzzification process, including without limitation Mean of Max defuzzification, Centroid of Area/Center of Gravity defuzzification, Center Average defuzzification, Bisector of Area defuzzification, or the like. Alternatively or additionally, output rules may be replaced with functions according to the Takagi-Sugeno-King (TSK) fuzzy model.

Further referring to FIG. 5, unimodal predictions to be used may be selected by user selection, and/or by selection of a distribution of output scores, such as 50% high durability, 40% moderate durability, and 50% low durability or the like. Each PFA durability categorization may be selected using an additional function such as in PFA durability as described above.

Figure 6:
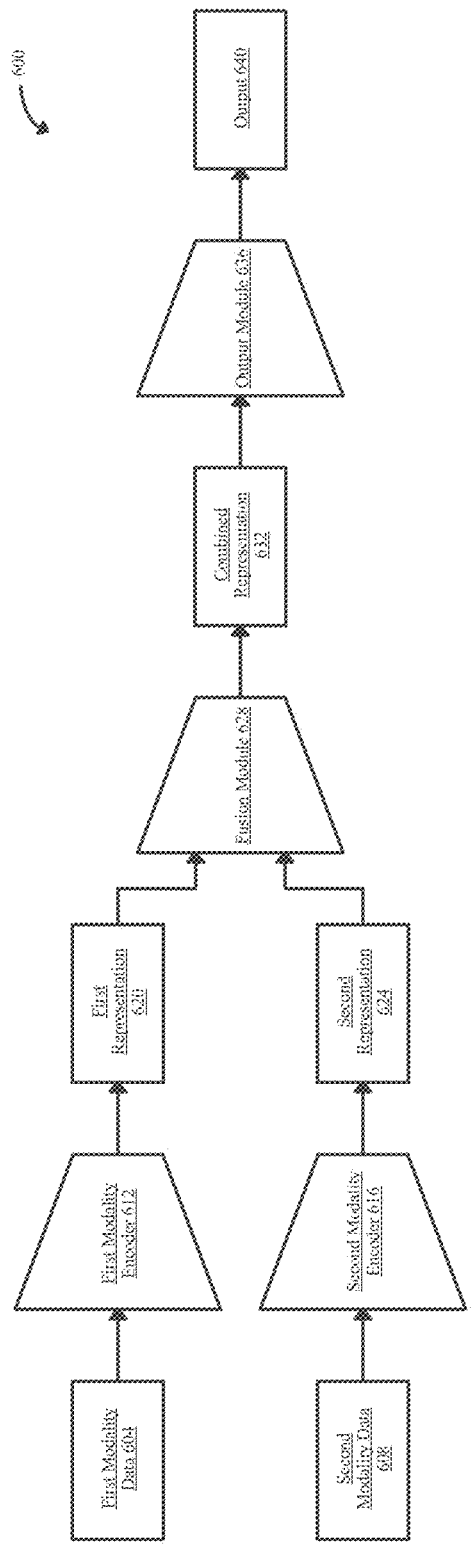
FIG. 6 is a block diagram depicting an exemplary embodiment of a multimodal neural network.

Referring now to FIG. 6, a block diagram of an exemplary embodiment of a multimodal neural network 600 is provided. As used herein, a "multimodal neural network" is a set of one or more neural networks which together accept inputs of a plurality of modes. In some embodiments, inputs of a plurality of modes may be used to generate a single output. Multimodal neural network 600 may include first modality data 604 and second modality data 608. In some embodiments, first modality data 604 may include ECG data. In some embodiments, first modality data 604 may include in-procedure ECG data. In some embodiments, first modality data 608 may include EGM data. In some embodiments, first modality data 608 may include in-procedure EGM data. Such data may be of different modes. Non-limiting examples of differing modalities include image data, text data, and audio data. In some embodiments, a multimodal neural network may include a plurality of unimodal neural networks, such as first modality encoder 612 and second modality encoder 616. Each such unimodal neural network may accept an input of a single mode and may output an encoding of such input. Outputs of such unimodal neural networks may include mathematical representations of the input data. An encoder may be chosen according to the type of data to be encoded. First modality encoder 612 may output first representation 620 and second modality encoder 616 may output second representation 624. Fusion module 628 may be used to join information of a plurality of modalities. Fusion module 628 may include, in non-limiting examples, concatenation of first representation 620 and second representation 624, taking weighted sums of first representation 620 and second representation 624, application of a transformer network, and application of an attention based recurrent neural network. Fusion module 628 may output combined representation 632. In some embodiments, a cross-attention layer mechanism may be used to generate combined representation 632. In some embodiments, multimodal neural network 600 may accept as inputs data of more than 2 modalities, and multiple cross-attention mechanisms may be used. For example, if representations of data of a first, second, and third modality are used, then cross-attention mechanisms may be used to capture interactions between the first and second modalities, between the first and third modalities, between the second and third modalities, and between the first, second and third modalities. Combined representation 632 may be input into output module 636 in order to produce output 640. Output 640 may include, for example, a PFA durability datum. Output module 636 may include a machine learning model such as a neural network.

Still referring to FIG. 6, in some embodiments, a multimodal neural network may include an alignment module. An alignment module may cause generated representations to be similar across different input modalities. In some embodiments, a multimodal neural network may include a translation module. A translation module may be used to map data of a first modality to a second modality. In some embodiments, a multimodal neural network may be trained using co-learning. Co-learning may include transfer of information across modalities when training a model.

Still referring to FIG. 6, in some embodiments, a multimodal neural network may function by making a plurality of predictions based on data of a single modality and combining such predictions. For example, voting schemes or weighted averages may be used to determine a multimodal prediction from a plurality of unimodal predictions.

Figure 7:
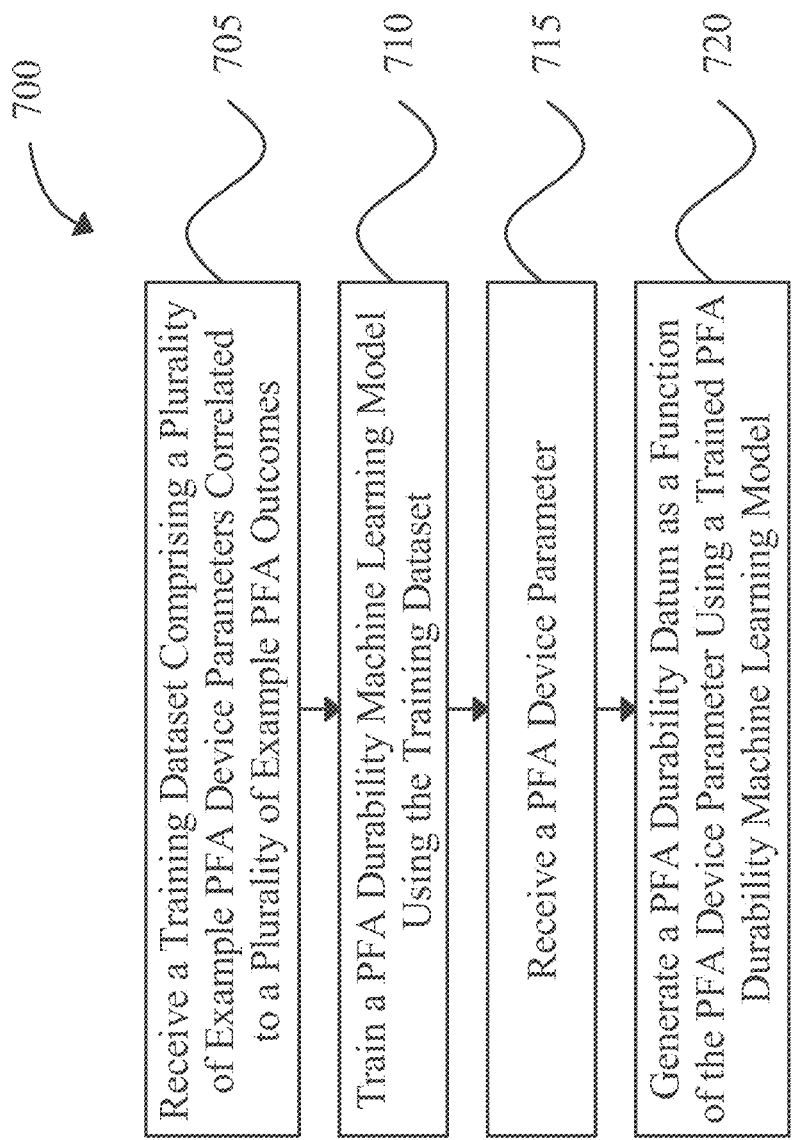
FIG. 7 is a flow diagram depicting an exemplary embodiment of a method of predicting Pulsed Field Ablation (PFA) durability.

Referring now to FIG. 7, an exemplary embodiment of a method 700 of predicting Pulsed Field Ablation (PFA) durability is illustrated. One or more steps if method 700 may be implemented, without limitation, as described with reference to other figures. One or more steps of method 700 may be implemented, without limitation, using at least a processor.

Still referring to FIG. 7, in some embodiments, method 700 may include receiving a training dataset comprising a plurality of example PFA device parameters correlated to a plurality of example PFA outcomes 705. In some embodiments, the example PFA outcomes comprise arterial fibrillation (AFib) recurrence data. In some embodiments, the example PFA outcomes comprise AFib burden data. In some embodiments, the example PFA outcomes comprise historical post-PFA procedure ECG data.

Still referring to FIG. 7, in some embodiments, method 700 may include training a PFA durability machine learning model using the training dataset 710.

Still referring to FIG. 7, in some embodiments, method 700 may include receiving a PFA device parameter 715. In some embodiments, the PFA device parameter is selected from the list consisting of voltage, pulse duration, frequency, pulse width, amplitude, power of ablation, total energy delivered, total treatment time, energy delivered to a particular location, treatment time at a particular location, current, average power, peak power, and pulse delivery phase (e.g., biphasic vs monophasic pulse delivery).

Still referring to FIG. 7, in some embodiments, method 700 may include generating a PFA durability datum as a function of the PFA device parameter using a trained PFA durability machine learning model 720. In some embodiments, the training dataset further comprises a plurality of example subject demographic information, correlated to the example PFA outcomes; and the PFA durability datum is generated as a function of the PFA device parameter and subject demographic information using the trained PFA durability machine learning model. In some embodiments, the training data further comprises example ECG data; the method further comprising receiving an ECG datum; and the PFA durability datum is generated as a function of the PFA device parameter and the ECG datum using the trained PFA durability machine learning model. In some embodiments, the PFA durability machine learning model comprises a neural network. In some embodiments, the PFA durability machine learning model comprises a multimodal neural network. In some embodiments, a subject whose PFA durability is estimated by the PFA durability datum has atrial fibrillation.

An apparatus, method, or feature thereof described herein may be consistent with any apparatus, method, or feature thereof disclosed in U.S. Pat. App. No. 63/614,858, filed on Dec. 26, 2023, and titled "SYSTEM AND METHOD FOR CLINICAL DECISION SUPPORT," the entirety of each of which is hereby incorporated by reference.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
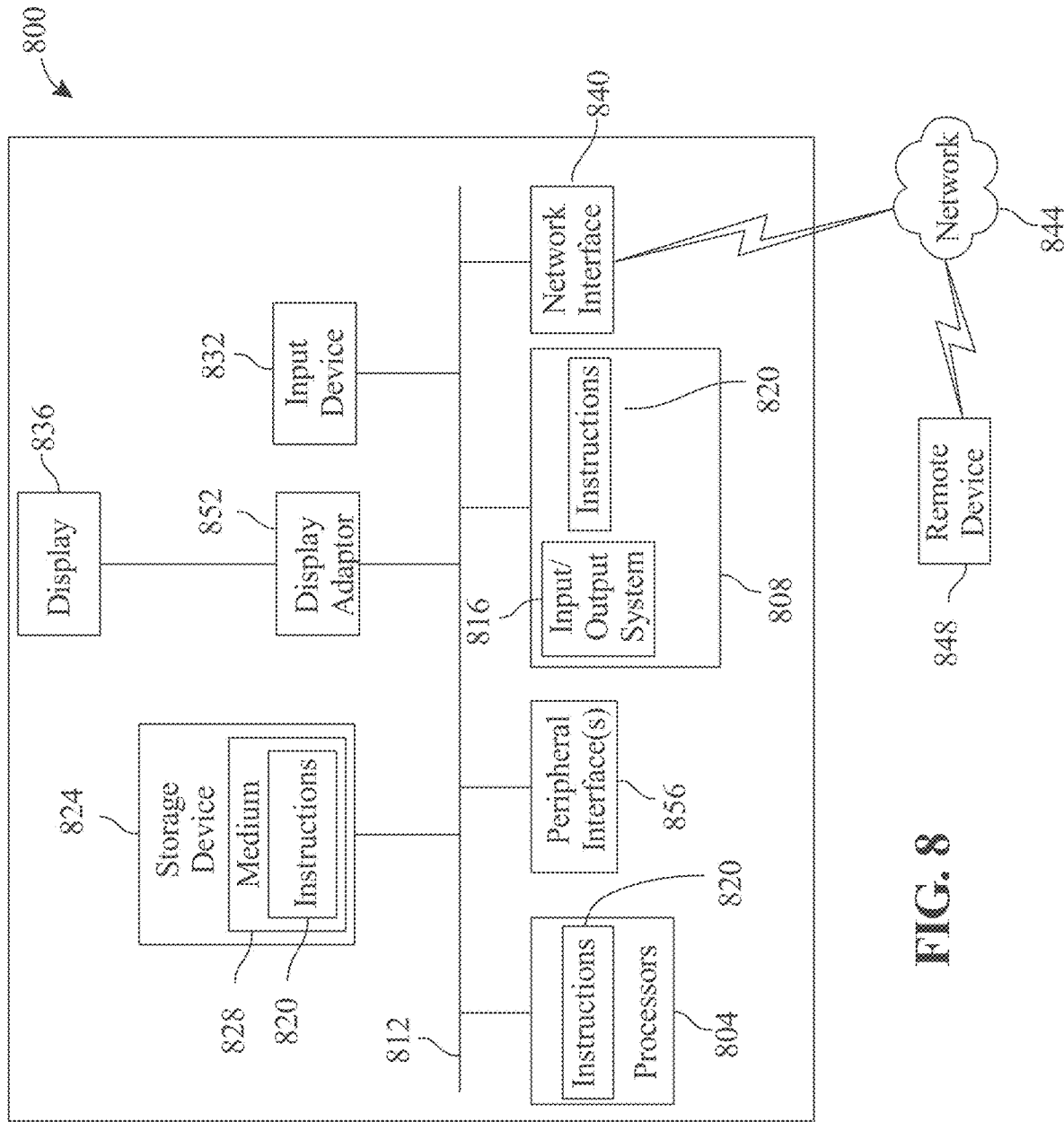
FIG. 8 is a block diagram of a computing system that can be used to implement any one or more of the methodologies disclosed herein and any one or more portions thereof.

FIG. 8 shows a diagrammatic representation of one embodiment of a computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Processor 804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIREWIRE interface, a direct interface to bus 812, and any combinations thereof. Input device 832 may include a touch screen interface that may be a part of or separate from display device 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for predicting Pulsed Field Ablation (PFA) durability, the apparatus comprising:
   at least a processor; and
   a memory communicatively connected to the at least processor, wherein the memory contains instructions configuring the at least processor to:
      receive a training dataset comprising a plurality of example PFA device parameters correlated to a plurality of example PFA outcomes;
      train a PFA durability machine learning model using the training dataset;
      receive a PFA device parameter; and
      generate a PFA durability datum as a function of the PFA device parameter using a trained PFA durability machine learning model.

2. The apparatus of claim 1, wherein the example PFA outcomes comprise arterial fibrillation (AFib) recurrence data.

3. The apparatus of claim 1, wherein the example PFA outcomes comprise AFib burden data.

4. The apparatus of claim 1, wherein the example PFA outcomes comprise historical post-PFA procedure ECG data.

5. The apparatus of claim 4, wherein the historical post-PFA procedure ECG data comprises historical post-PFA procedure ECG data captured at least 1 day after, 2 days after, 3 days after, 4 days after, 5 days after, 6 days after, 1 week after, 2 weeks after, 3 weeks after, 4 weeks after, 6 weeks after, 2 months after, 3 months after, 6 months after, 9 months after, 1 year after, 2 years after, or 2 years after a historical PFA procedure.

6. The apparatus of claim 1, wherein:
   the training dataset further comprises a plurality of example subject demographic information correlated to the example PFA outcomes; and
   the memory contains instructions configuring the at least processor to generate the PFA durability datum as a function of the PFA device parameter and subject demographic information using the trained PFA durability machine learning model.

7. The apparatus of claim 1, wherein the PFA device parameter is of a type selected from a list consisting of voltage, pulse duration, frequency, pulse width, amplitude, power of ablation, total energy delivered, total treatment time, energy delivered to a particular location, treatment time at a particular location, current, average power, peak power, and pulse delivery phase.

8. The apparatus of claim 1, wherein:
   the training data further comprises example ECG data;
   the memory contains instructions configuring the at least a processor to receive at least an ECG datum; and
   the memory contains instructions configuring the at least a processor to generate the PFA durability datum as a function of the PFA device parameter and the at least an ECG datum using the trained PFA durability machine learning model.

9. The apparatus of claim 1, wherein the training dataset further comprises in-procedure ECG data and in-procedure EGM data.

10. The apparatus of claim 1, wherein the PFA durability machine learning model comprises a multimodal neural network.

11. A method of predicting Pulsed Field Ablation (PFA) durability, the method comprising:
    using at least a processor, receiving a training dataset comprising a plurality of example PFA device parameters correlated to a plurality of example PFA outcomes;
    using the at least a processor, training a PFA durability machine learning model using the training dataset;
    using the at least a processor, receiving a PFA device parameter; and
    using the at least a processor, generating a PFA durability datum as a function of the PFA device parameter using a trained PFA durability machine learning model.

12. The method of claim 11, wherein the example PFA outcomes comprise arterial fibrillation (AFib) recurrence data.

13. The method of claim 11, wherein the example PFA outcomes comprise AFib burden data.

14. The method of claim 11, wherein the example PFA outcomes comprise historical post-PFA procedure ECG data.

15. The method of claim 14, wherein the historical post-PFA procedure ECG data comprises historical post-PFA procedure ECG data captured at least 1 day after, 2 days after, 3 days after, 4 days after, 5 days after, 6 days after, 1 week after, 2 weeks after, 3 weeks after, 4 weeks after, 6 weeks after, 2 months after, 3 months after, 6 months after, 9 months after, 1 year after, 2 years after, or 2 years after a historical PFA procedure.

16. The method of claim 11, wherein:
the training dataset further comprises a plurality of example subject demographic information correlated to the example PFA outcomes; and
the PFA durability datum is generated as a function of the PFA device parameter and subject demographic information using the trained PFA durability machine learning model.

17. The method of claim 11, wherein the PFA device parameter is of a type selected from a list consisting of voltage, pulse duration, frequency, pulse width, amplitude, power of ablation, total energy delivered, total treatment time, energy delivered to a particular location, treatment time at a particular location, current, average power, peak power, and pulse delivery phase.

18. The method of claim 11, wherein:
the training data further comprises example ECG data;
the method further comprising receiving at least an ECG datum; and
the PFA durability datum is generated as a function of the PFA device parameter and the at least an ECG datum using the trained PFA durability machine learning model.

19. The method of claim 11, wherein the training dataset further comprises in-procedure ECG data and in-procedure EGM data.

20. The method of claim 11, wherein the PFA durability machine learning model comprises a multimodal neural network.

\* \* \* \* \*